(12) United States Patent
LaBorde

(10) Patent No.: US 12,217,841 B1
(45) Date of Patent: *Feb. 4, 2025

(54) SYSTEM, RFID CHIP, SERVER AND METHOD FOR CAPTURING VEHICLE DATA

(71) Applicant: Brain Trust Innovations I, LLC, Alpharetta, GA (US)

(72) Inventor: David LaBorde, Alpharetta, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 130 days.

This patent is subject to a terminal disclaimer.

(21) Appl. No.: 18/150,749

(22) Filed: Jan. 5, 2023

Related U.S. Application Data

(63) Continuation of application No. 16/852,397, filed on Apr. 17, 2020, now Pat. No. 11,756,660, which is a
(Continued)

(51) Int. Cl.
*H04W 4/02* (2018.01)
*G01C 21/34* (2006.01)
(Continued)

(52) U.S. Cl.
CPC ......... *G16H 10/65* (2018.01); *G01C 21/3476* (2013.01); *G05D 1/0088* (2013.01);
(Continued)

(58) Field of Classification Search
CPC ...... G16H 10/65; G16H 40/63; G05D 1/0088; G06F 17/11; G06K 7/10366; G06N 3/04;
(Continued)

(56) References Cited

U.S. PATENT DOCUMENTS

| 3,953,720 A | 4/1976 | Kelch |
| 4,092,718 A | 5/1978 | Wendt |

(Continued)

FOREIGN PATENT DOCUMENTS

| CN | 102402852 | 4/2012 |
| CN | 102496265 | 6/2012 |

(Continued)

OTHER PUBLICATIONS

Pivato et al., "Experimental Assessment of a RSS-based Localization Algorithm in Indoor Environment", [online], May 2010 [retrieved on Sep. 4, 2015]. Retrieved from the Internet: <URL:http://www.researchgate.net/profile/Paolo_Pivato/publication/224146714_Experimental_Assessment_of_a_RSS-based_Localization_Algorithm_in_Indoor_Environment/links/0912f502b6b29f22ea000000.pdf>.

(Continued)

*Primary Examiner* — Khoi V Le
(74) *Attorney, Agent, or Firm* — Culpepper IP, LLLC; Kerry S. Culpepper

(57) ABSTRACT

A system includes a plurality of tracking devices, such as RFID tags, affixed to items, such as vehicles, a data collection engine, client devices and backend devices. The backend devices include trained machine learning models, business logic, and attributes of a plurality of events. A plurality of data collection engines and systems send attributes of new events to the backend devices. The backend devices can track the items and predict particular outcomes of new events based upon the attributes of the new events utilizing the trained machine learning models.

17 Claims, 26 Drawing Sheets

Related U.S. Application Data continuation of application No. 16/578,942, filed on Sep. 23, 2019, now Pat. No. 10,628,739, which is a continuation of application No. 16/231,832, filed on Dec. 24, 2018, now Pat. No. 10,482,377, which is a continuation of application No. 16/012,088, filed on Jun. 19, 2018, now Pat. No. 10,176,891, which is a continuation of application No. 15/934,966, filed on Mar. 24, 2018, now Pat. No. 10,026,506, which is a continuation-in-part of application No. 15/704,494, filed on Sep. 14, 2017, now Pat. No. 9,928,342, which is a continuation-in-part of application No. 15/592,116, filed on May 10, 2017, now Pat. No. 9,848,827, which is a continuation of application No. 15/390,695, filed on Dec. 26, 2016, now Pat. No. 9,679,108, which is a continuation of application No. 15/004,535, filed on Jan. 22, 2016, now Pat. No. 9,569,589.

(60) Provisional application No. 62/113,356, filed on Feb. 6, 2015.

(51) Int. Cl.
| | | |
|---|---|---|
| *G05D 1/00* | (2006.01) | |
| *G06F 17/11* | (2006.01) | |
| *G06K 7/10* | (2006.01) | |
| *G06N 3/04* | (2023.01) | |
| *G06N 3/048* | (2023.01) | |
| *G06N 3/08* | (2023.01) | |
| *G06N 3/088* | (2023.01) | |
| *G16H 10/65* | (2018.01) | |
| *G16H 40/63* | (2018.01) | |
| *G06N 3/006* | (2023.01) | |
| *G06N 3/044* | (2023.01) | |
| *G06N 3/047* | (2023.01) | |
| *G06N 3/084* | (2023.01) | |
| *G06N 3/086* | (2023.01) | |
| *G06N 3/126* | (2023.01) | |
| *G06N 5/01* | (2023.01) | |
| *G06N 5/048* | (2023.01) | |
| *G06N 7/01* | (2023.01) | |
| *G06N 20/10* | (2019.01) | |

(52) U.S. Cl.
CPC .......... *G06F 17/11* (2013.01); *G06K 7/10366* (2013.01); *G06N 3/04* (2013.01); *G06N 3/048* (2023.01); *G06N 3/08* (2013.01); *G06N 3/088* (2013.01); *G16H 40/63* (2018.01); *H04W 4/02* (2013.01); *G06N 3/006* (2013.01); *G06N 3/0409* (2013.01); *G06N 3/044* (2023.01); *G06N 3/047* (2023.01); *G06N 3/084* (2013.01); *G06N 3/086* (2013.01); *G06N 3/126* (2013.01); *G06N 5/01* (2023.01); *G06N 5/048* (2013.01); *G06N 7/01* (2023.01); *G06N 20/10* (2019.01)

(58) Field of Classification Search
CPC ........ G06N 3/0481; G06N 3/08; G06N 3/088; G06N 3/006; G06N 3/0409; G06N 3/0445; G06N 3/0472; G06N 3/084; H04W 4/02

See application file for complete search history.

(56) References Cited

U.S. PATENT DOCUMENTS

| | | |
|---|---|---|
| 4,360,875 A | 11/1982 | Behnke |
| 5,043,736 A | 8/1991 | Darnell |
| 5,168,451 A | 12/1992 | Bolger |
| 5,293,642 A | 3/1994 | Lo |
| 5,519,760 A | 5/1996 | Borkowski et al. |
| 5,604,676 A | 2/1997 | Penzias |
| 5,625,668 A | 4/1997 | Loomis et al. |
| 5,799,263 A | 8/1998 | Culbertson |
| 5,862,244 A | 1/1999 | Kleiner et al. |
| 5,930,474 A | 7/1999 | Dunworth et al. |
| 6,356,838 B1 | 3/2002 | Paul |
| 6,446,004 B1 | 9/2002 | Cao |
| 6,456,207 B1 | 9/2002 | Yen |
| 6,456,852 B2 | 9/2002 | Bar |
| 6,516,056 B1 | 2/2003 | Justice et al. |
| 6,519,463 B2 | 2/2003 | Tendler |
| 6,591,253 B1 | 7/2003 | Dinkin |
| 6,697,730 B2 | 2/2004 | Dickerson |
| 6,756,913 B1 | 6/2004 | Ayed |
| 6,804,658 B2 | 10/2004 | Lim et al. |
| 6,925,381 B2 | 8/2005 | Adamczyk |
| 7,064,681 B2 | 6/2006 | Horstmeyer |
| 7,089,110 B2 | 8/2006 | Pechatnikov et al. |
| 7,113,110 B2 | 9/2006 | Horstmeyer |
| 7,119,716 B2 | 10/2006 | Horstmeyer |
| 7,158,030 B2 | 1/2007 | Chung |
| 7,191,057 B2 | 3/2007 | Adamcyzk |
| 7,315,780 B2 | 1/2008 | Sugahara et al. |
| 7,319,414 B2 | 1/2008 | Horstmeyer |
| 7,388,506 B2 | 6/2008 | Abbott |
| 7,394,386 B2 | 7/2008 | Nowlan |
| 7,412,042 B2 | 8/2008 | Henry |
| 7,434,177 B1 | 10/2008 | Ording et al. |
| 7,479,887 B2 | 1/2009 | Meyer |
| 7,479,899 B2 | 1/2009 | Horstmeyer |
| 7,479,900 B2 | 1/2009 | Horstmeyer |
| 7,479,901 B2 | 1/2009 | Horstmeyer |
| 7,487,467 B1 | 2/2009 | Kawahara et al. |
| 7,504,966 B2 | 3/2009 | Horstmeyer |
| 7,528,742 B2 | 5/2009 | Horstmeyer |
| 7,538,691 B2 | 5/2009 | Horstmeyer |
| 7,482,952 B2 | 6/2009 | Horstmeyer |
| 7,552,063 B1 | 6/2009 | McEachern |
| 7,561,069 B2 | 7/2009 | Horstmeyer |
| 7,586,417 B2 | 9/2009 | Chisholm |
| 7,673,251 B1 | 3/2010 | Wibisono |
| 7,756,633 B2 | 7/2010 | Huang |
| 7,772,981 B1 | 8/2010 | Lambert et al. |
| 7,850,893 B2 | 12/2010 | Chisholm et al. |
| 7,852,221 B2 | 12/2010 | Tuttle |
| 7,864,935 B2 | 1/2011 | Elliott |
| 7,869,945 B2 | 1/2011 | Huang |
| 7,875,227 B2 | 1/2011 | Chisholm |
| 7,876,239 B2 | 1/2011 | Horstmeyer |
| 7,922,961 B2 | 4/2011 | Chisholm et al. |
| 7,970,533 B2 | 6/2011 | Huang |
| 7,973,664 B1 | 7/2011 | Lambert et al. |
| 7,974,779 B2 | 7/2011 | Huang |
| 8,036,824 B2 | 10/2011 | Huang |
| 8,068,037 B2 | 11/2011 | Horstmeyer |
| 8,086,400 B2 | 12/2011 | Huang |
| 8,097,199 B2 | 1/2012 | Abbott et al. |
| 8,098,162 B2 | 1/2012 | Abbott et al. |
| 8,120,484 B2 | 2/2012 | Chisholm |
| 8,140,256 B1 | 3/2012 | dos-Santos |
| 8,181,875 B2 | 5/2012 | Nishido |
| 8,212,226 B2 | 7/2012 | Chisholm |
| 8,224,571 B2 | 7/2012 | Huang |
| 8,232,899 B2 | 7/2012 | Horstmeyer |
| 8,242,935 B2 | 8/2012 | Horstmeyer |
| 8,271,316 B2 | 9/2012 | Blackshaw et al. |
| 8,284,076 B1 | 10/2012 | Horstmeyer |
| 8,296,247 B2 | 10/2012 | Zhang et al. |
| 8,362,927 B2 | 1/2013 | Horstmeyer |
| 8,368,562 B2 | 2/2013 | Horstmeyer |
| 8,374,627 B2 | 2/2013 | Howard et al. |
| 8,386,593 B1 | 2/2013 | Gao |
| 8,478,535 B2 | 7/2013 | Jojic et al. |
| 8,531,317 B2 | 9/2013 | Horstmeyer |
| 8,554,608 B1 | 10/2013 | O'Connor |
| 8,564,459 B2 | 10/2013 | Horstmeyer |

(56) References Cited

U.S. PATENT DOCUMENTS

| | | |
|---|---|---|
| 2002/0034292 A1 | 3/2002 | Tuoriniemi |
| 2002/0077905 A1 | 6/2002 | Arndt |
| 2002/0095326 A1 | 7/2002 | Katz |
| 2002/0138338 A1 | 9/2002 | Trauth et al. |
| 2002/0194129 A1 | 12/2002 | Furuya et al. |
| 2003/0040944 A1 | 2/2003 | Hileman |
| 2003/0043206 A1 | 3/2003 | Duarte |
| 2003/0087648 A1 | 5/2003 | Mezhvinsky et al. |
| 2003/0137435 A1 | 7/2003 | Haddad |
| 2004/0054428 A1 | 3/2004 | Sheha et al. |
| 2004/0093280 A1 | 5/2004 | Yamaguchi |
| 2004/0100479 A1 | 5/2004 | Nakano et al. |
| 2004/0106399 A1 | 6/2004 | Ki |
| 2004/0112959 A1 | 6/2004 | Jun |
| 2004/0155907 A1 | 8/2004 | Yamaguchi |
| 2004/0158483 A1 | 8/2004 | LeCouturier |
| 2004/0185842 A1 | 9/2004 | Spaur et al. |
| 2004/0219933 A1 | 11/2004 | Faith |
| 2004/0243430 A1 | 12/2004 | Horstmeyer |
| 2004/0254717 A1 | 12/2004 | Sugahara et al. |
| 2004/0254811 A1 | 12/2004 | Horstmeyer |
| 2005/0091596 A1 | 4/2005 | Anthony et al. |
| 2005/0149382 A1 | 7/2005 | Fenner et al. |
| 2005/0227704 A1 | 10/2005 | Ferra et al. |
| 2005/0278063 A1 | 12/2005 | Hersh et al. |
| 2005/0278114 A1 | 12/2005 | Ahmad |
| 2006/0034201 A1 | 2/2006 | Umeda et al. |
| 2006/0048076 A1 | 3/2006 | Vronay et al. |
| 2006/0059023 A1 | 3/2006 | Mashinsky |
| 2006/0094447 A1 | 5/2006 | Zellner |
| 2006/0135134 A1 | 6/2006 | Mezhvinsky et al. |
| 2006/0136254 A1 | 6/2006 | Greenstein |
| 2006/0149681 A1 | 7/2006 | Meisner |
| 2006/0161346 A1 | 7/2006 | Murakami et al. |
| 2006/0178949 A1 | 8/2006 | McGrath |
| 2006/0200306 A1 | 9/2006 | Adamcyzk |
| 2006/0200396 A1 | 9/2006 | Adamcyzk |
| 2006/0217885 A1 | 9/2006 | Crady et al. |
| 2006/0229778 A1 | 10/2006 | Obradovich et al. |
| 2006/0268100 A1 | 11/2006 | Karukka et al. |
| 2006/0271867 A1 | 11/2006 | Wang et al. |
| 2007/0073477 A1 | 3/2007 | Krumm et al. |
| 2007/0103342 A1 | 5/2007 | Milleville |
| 2007/0176796 A1 | 8/2007 | Bliss et al. |
| 2007/0197229 A1 | 8/2007 | Kalliola |
| 2007/0198276 A1 | 8/2007 | Hinrichs et al. |
| 2008/0068171 A1 | 3/2008 | Ehrman et al. |
| 2008/0070593 A1 | 3/2008 | Altman |
| 2008/0076451 A1 | 3/2008 | Sheha et al. |
| 2008/0114629 A1 | 5/2008 | Pavlov |
| 2008/0125967 A1 | 5/2008 | Sprigg |
| 2008/0169937 A1 | 7/2008 | Lowry |
| 2008/0172173 A1 | 7/2008 | Chang et al. |
| 2008/0178116 A1 | 7/2008 | Kim |
| 2008/0189207 A1 | 8/2008 | Wurster |
| 2008/0195428 A1 | 8/2008 | O'Sullivan |
| 2008/0270019 A1 | 10/2008 | Anderson |
| 2008/0288880 A1 | 11/2008 | Reponen et al. |
| 2008/0307512 A1 | 12/2008 | Tandon |
| 2009/0030885 A1 | 1/2009 | De Pasquale et al. |
| 2009/0049119 A1 | 2/2009 | Marcinkiewicz et al. |
| 2009/0083111 A1 | 3/2009 | Carr |
| 2009/0099971 A1 | 4/2009 | Salemme et al. |
| 2009/0106124 A1 | 4/2009 | Yang |
| 2009/0156241 A1 | 6/2009 | Staffaroni et al. |
| 2009/0171529 A1 | 7/2009 | Hayatoma |
| 2009/0171576 A1 | 7/2009 | Kim et al. |
| 2009/0172599 A1 | 7/2009 | Nezu |
| 2009/0176508 A1 | 7/2009 | Lubeck et al. |
| 2009/0177384 A1 | 7/2009 | Walder |
| 2009/0177385 A1 | 7/2009 | Matas et al. |
| 2009/0177502 A1 | 7/2009 | Doinoff et al. |
| 2009/0187538 A1 | 7/2009 | Grun |
| 2009/0192851 A1 | 7/2009 | Bishop |
| 2009/0204920 A1 | 8/2009 | Beverley et al. |
| 2009/0216600 A1 | 8/2009 | Hill |
| 2009/0222284 A1 | 9/2009 | McEachern |
| 2009/0254270 A1 | 10/2009 | Yu |
| 2009/0282353 A1 | 11/2009 | Halbherr et al. |
| 2009/0313077 A1 | 12/2009 | Wheeler, IV |
| 2009/0326991 A1 | 12/2009 | Wei |
| 2010/0023246 A1 | 1/2010 | Zhao |
| 2010/0035596 A1 | 2/2010 | Nachman et al. |
| 2010/0070334 A1 | 3/2010 | Monteverde |
| 2010/0076988 A1 | 3/2010 | Kenedy et al. |
| 2010/0115455 A1 | 5/2010 | Kim |
| 2010/0121689 A1 | 5/2010 | Wallace |
| 2010/0153292 A1 | 6/2010 | Zheng et al. |
| 2010/0182265 A1 | 7/2010 | Kim |
| 2010/0190436 A1 | 7/2010 | Cook et al. |
| 2010/0198453 A1 | 8/2010 | Dorogusker |
| 2010/0199213 A1 | 8/2010 | Suzuki |
| 2010/0235085 A1 | 9/2010 | Kikuchi |
| 2010/0243724 A1 | 9/2010 | Golla |
| 2010/0228415 A1 | 11/2010 | Paul |
| 2010/0299436 A1 | 11/2010 | Khalid |
| 2011/0010300 A1 | 1/2011 | Audet |
| 2011/0035139 A1* | 2/2011 | Konlditslotis ......... G08G 1/207 |
| | | 701/119 |
| 2011/0050588 A1 | 3/2011 | Li |
| 2011/0052110 A1 | 3/2011 | Kim |
| 2011/0060480 A1 | 3/2011 | Mattia et al. |
| 2011/0099040 A1 | 4/2011 | Felt |
| 2011/0060600 A1 | 5/2011 | Fox et al. |
| 2011/0137696 A1 | 6/2011 | Meyer et al. |
| 2011/0137699 A1 | 6/2011 | Ronen et al. |
| 2011/0153192 A1 | 6/2011 | Lin |
| 2011/0153453 A1 | 6/2011 | Ghafoor |
| 2011/0208732 A1 | 8/2011 | Melton et al. |
| 2011/0218992 A1 | 9/2011 | Waldman et al. |
| 2011/0221765 A1 | 9/2011 | Nason et al. |
| 2011/0291809 A1 | 12/2011 | Niemiec |
| 2011/0301795 A1* | 12/2011 | Failing .................. B60L 53/126 |
| | | 701/45 |
| 2011/0313804 A1 | 12/2011 | Camp et al. |
| 2011/0313880 A1 | 12/2011 | Paul |
| 2012/0038474 A1* | 2/2012 | De Sanzo ............ B60Q 1/2607 |
| | | 340/468 |
| 2012/0041675 A1 | 2/2012 | Juliver |
| 2012/0084676 A1 | 4/2012 | de Paz |
| 2012/0130627 A1 | 5/2012 | Islam et al. |
| 2012/0131170 A1 | 5/2012 | Spat |
| 2012/0179764 A1 | 7/2012 | Erdal |
| 2012/0239452 A1 | 9/2012 | Trivedi et al. |
| 2012/0313965 A1 | 12/2012 | Mochizuki et al. |
| 2012/0327009 A1 | 12/2012 | Fleizach |
| 2013/0002034 A1 | 1/2013 | Onizuka et al. |
| 2013/0041720 A1 | 2/2013 | Spires |
| 2013/0162627 A1 | 6/2013 | Gabara |
| 2013/0204676 A1 | 8/2013 | Hindi et al. |
| 2013/0234849 A1 | 9/2013 | Gupta et al. |
| 2013/0246207 A1 | 9/2013 | Novak |
| 2014/0236778 A1* | 8/2014 | Villardito ............. G06Q 10/087 |
| | | 705/28 |
| 2015/0012341 A1 | 1/2015 | Amin |
| 2015/0046080 A1 | 2/2015 | Wesselius et al. |
| 2015/0219464 A1 | 8/2015 | Beaurepaire |
| 2015/0317589 A1 | 11/2015 | Anderson et al. |
| 2016/0019790 A1 | 1/2016 | Tobolski |
| 2017/0370734 A1 | 12/2017 | Cojin |
| 2018/0032690 A1 | 2/2018 | Perlman |

FOREIGN PATENT DOCUMENTS

| | | |
|---|---|---|
| CN | 102682593 | 9/2012 |
| GB | 2367979 | 4/2002 |
| JP | 2001/188996 | 7/2001 |
| JP | 2002/024659 | 1/2002 |
| KR | 10-2005-0015772 | 2/2005 |
| KR | 10-2009-0109044 | 10/2009 |
| KR | 10-1006599 | 1/2011 |
| WO | 98/00988 | 1/1998 |
| WO | 98/40837 | 9/1998 |

(56) References Cited

FOREIGN PATENT DOCUMENTS

| WO | 99/44186 | 9/1999 |
| WO | 2002/006994 | 1/2002 |
| WO | 2010056923 | 11/2009 |
| WO | 2010/015984 | 11/2010 |

OTHER PUBLICATIONS

Zafari et al., Micro-location for Internet of Things equipped Smart Buildings, [online], Jan. 7, 2015 [retrieved on Sep. 3, 2015]. Retrieved from the Internet:<URL:http://arxiv.org/abs/1501.01539>.

Bolic et al., "Proximity Detection with RFID: A Step Toward the Internet of Things", Apr. 23, 2015, Pervasive Computing IEEE, vol. 14 Issue:2, Published by IEEE.

Wong et al., "30 Years of Multidimensional Multivariate Visualization", [online], 1997 [retrieved on Aug. 12, 2016]. Retrieved from the Internet: <URL:http://citeseerx.ist.psu.edu/viewdoc/download?doi=10.1.1.30.4639&rep=rep1&type=pdf>.

Impinj, White Paper "New Thinking on an Old Challenge: Improving Healthcare Asset Management with RAIN RFID Technology", [online], 2017 [retrieved on Nov. 16, 2017]. Retrieved from the Internet: <URL:https://www.impinj.com/media/2046/impinj-healthcare-asset-management-white-paper.pdf>.

Erica Drazen, "Using Tracking Tools to Improve Patient Flow in Hosptals", [online], Apr. 2011 [retrieved on Feb. 15, 2018]. Retrieved from the Internet: <URL:https://www.chcf.org/publication/using-tracking-tools-to-improve-patient-flow-in-hospitals/>.

Leaf Healthcare, White Paper "Technical Overview of the Leaf Patient Monitoring System", [online], 2018 [retrieved on Mar. 19, 2018]. Retrieved from the Internet: <URL:http://www.leafhealthcare.com/pdfs/_H_WP_TechOverview_1564AB_030818.pdf>.

Leaf Healthcare, "A New Standard for Optimizing Patient Repositioning", [online], 2018 [retrieved on Mar. 19, 2018]. Retrieved from the Internet: <URL:http://www.leafhealthcare.com/solution.cfm#/s6>.

Suzanne Hodsden, "Smith & Nephew Integrates Wireless Patient Monitoring Into Wound Care Platform", Med Device Online, [online], Apr. 10, 2017 [retrieved on Mar. 19, 2018]. Retrieved from the Internet:<URL:https://www.meddeviceonline.com/doc/smith-nephew-integrates-wireless-patient-monitoring-into-wound-care-platform-0001>.

*Lyft Inc* v. *Rideapp, Inc.*, Case IPR2019-00671, Aug. 12, 2019.

*Lyft Inc* v. *Rideapp, Inc.*, 18-CV-07152-JST, United States District Court Northern District of California San Francisco Division, Doc. 93 Patent L.R. 4-3 Joint Claim Construction and Prehearing Statement Jul. 19, 2019.

\* cited by examiner

Exemplary Regression Task-Supervised Learning
(2D Example Shown for Simplicity)

SYSTEM, RFID CHIP, SERVER AND METHOD FOR CAPTURING VEHICLE DATA

CROSS-REFERENCE TO RELATED APPLICATIONS

The present application is a continuation of U.S. patent application Ser. No. 16/852,397 filed on Apr. 17, 2020, which is a continuation of U.S. patent application Ser. No. 16/578,942 filed on Sep. 23, 2019 now U.S. Pat. No. 10,628,739, which is a continuation of U.S. patent application Ser. No. 16/231,832 filed on Dec. 24, 2018 now U.S. Pat. No. 10,482,377, which is a continuation of U.S. patent application Ser. No. 16/012,088 filed on Jun. 19, 2018, which is a continuation of U.S. patent application Ser. No. 15/934,966 filed on Mar. 24, 2018 now U.S. Pat. No. 10,026,506, which is a continuation-in-part of U.S. patent application Ser. No. 15/704,494 filed on Sep. 14, 2017 now U.S. Pat. No. 9,928,342, which is a continuation-in-part of U.S. patent application Ser. No. 15/592,116 filed on May 10, 2017 now U.S. Pat. No. 9,848,827, which is a continuation of U.S. patent application Ser. No. 15/390,695 filed on Dec. 26, 2016 now U.S. Pat. No. 9,679,108, which is a continuation of U.S. patent application Ser. No. 15/004,535 filed on Jan. 22, 2016 now U.S. Pat. No. 9,569,589, which claims the benefit of U.S. Provisional Patent Application No. 62/113,356 filed on Feb. 6, 2015, the contents all of which are incorporated herein by reference.

TECHNICAL FIELD

The technical field generally relates to a system including a data collection engine, a plurality of vehicles including radio-frequency identification chips or other tracking devices, and a server device.

BACKGROUND

A radio-frequency Identification (RFID) chip can transmit information to a reader in response to an interrogation signal or polling request from the reader. The RFID chip can be incorporated in a tag (RFID tag) which is placed on items such as a vehicle so that information can be passively captured. In this disclosure the term item will be used generally to refer to vehicles, identifications, etc.

An RFID tag can be an active-type with its own power source, or a passive-type or battery-assisted passive type with no or limited power source. Both the passive-type and battery-assisted passive type will be referred to here as passive-type for sake of brevity. Placing an active-type RFID tag on some items may not be feasible do to financial considerations, weight, etc. On the other hand, placing a passive-type RFID tag on items may be more feasible; however, a power source will be needed to passively obtain information. Therefore, a device that can provide power to the RFID tag on the item as well as obtain the information from the RFID tag would be beneficial.

Autonomous vehicles, such as vehicles that do not require a human driver, can be used to aid in the transport of passengers or items from one location to another. Such vehicles may operate in a fully autonomous mode where passengers may provide some initial input, such as pick up or destination location, and the vehicle maneuvers itself to that location.

SUMMARY

A system that can accurately track the path of vehicles and determine which vehicles are most suitable for a pick-up request would be preferable. It would be further preferable if such a system could take advantage of artificial intelligence techniques such as machine learning and self-organizing maps to predict travel routes and travel times for the vehicle. It would be further preferable if such as system could leverage this data to calculate an appropriate charge for the pick-up request.

According to various embodiments, a system includes tracking devices associated with items such as vehicles and/or identifications of vehicle drivers, and a server device. In one embodiment, the tracking device can be a data collection engine (DCE) and an RFID chip associated with the item. The RFID chip can be incorporated in a tag (RFID tag) which is placed in the vehicle. An RFID tag can be an active-type with its own power source, or a passive-type or battery-assisted passive type with no or limited power source. In one embodiment, the tracking device can be a mobile device such as a smartphone.

Instructions configure the server device controller to: create a model such as a neural network model (NNM) for modeling events; train and validate the NNM by supervised learning; calculate an output value for new events based upon the trained NNM; and classify the output value. For example, the event can be a pick-up request accepted by a vehicle with certain parameters (driver identity, speed, time, location, etc.) and classification of the output value can be a Boolean value such as the vehicle deviated from expected arrival time, a predicted time of arrival of the vehicle at the pick-up request and/or a drop-off location associated with the pick-up request.

Input attributes of the events can be origination, destination, time to route, dateTime start, dateTime end, gps data collected periodically through route, driver identity (from known association with mobile device, RFID tag, pick-up request originator identity, current density of pick-up requests, price paid per mile, price paid per unit time, price accepted/price rejected, etc.

The instructions can also configure the controller to create a self-organizing map (SOM) network for modeling events, the SOM including a plurality of network nodes, a plurality of input nodes representing input attributes of the past events, wherein the plurality of network nodes is arranged in a grid or lattice in a fixed topological position, each of the plurality of input nodes is connected to all of the plurality of network nodes by a plurality of synaptic weights. The controller can generate an output value of the SOM network based upon input attributes for the event, wherein the output value is a graphical display showing a particular category for the event.

According to various embodiments, a system includes a plurality of mobile devices such as smartphones in the vehicles, a server device and a client device. The smartphone in a respective one of the vehicles transmits the vehicle identification and location to the server device. A client device can send a request to the server device to request a pick up. The server device can determine which of the vehicles should be assigned to handle the request for a pick up. The location information can be GPS information from the smartphone or from a base station in communication with the smartphone.

The system can store map information indicative of (i) particular locations that are accessible for the vehicles to pick up or drop off passengers and locations that are not accessible and (ii) routes or travel paths that are not accessible for the vehicles. Alternatively, the system can obtain the map information from third party sources.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

DETAILED DESCRIPTION

In overview, the present disclosure concerns a system which includes a Data Collection Engine (DCE), an RFID tag associated with items such as, for example, vehicles, identifications of vehicle drivers, backend devices such as one or more server devices and a throughput management device (TMD), and a plurality of client devices.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
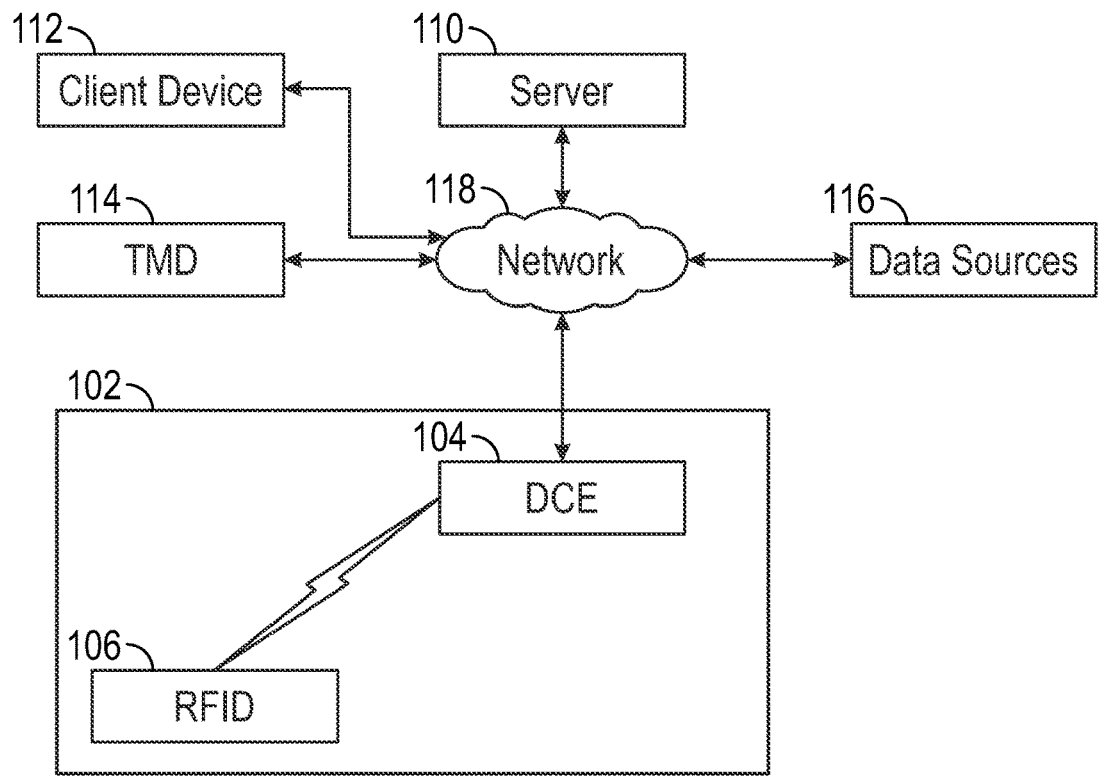
FIG. 1 illustrates an exemplary core operating environment in which a Data Collection Engine (DCE) receives data from an RFID tag and transmits the data to a server device via a connection to a network, a throughput management device (TMD) and client device exchange data with the server device via a connection to the network and the server device receives data from data sources via the connection.

Referring to FIG. 1, an exemplary operating environment in which the system according to various embodiments can be implemented will be discussed. The environment includes an item 102, such as a vehicle, which includes a DCE 104 communicating with RFID tag 106. As discussed more fully below, the communication between the RFID tag 106 and the DCE 104 is preferably wireless; however, wireline communication or a combination of wireless and wireline communication can also be used in some cases. The DCE 104, although shown here as a single entity, can include sub-portions. The DCE 104 communicates with one or more server devices (represented generally by and referred to hereon as "server") 110 via a connection to a network 108 such as a local area network (LAN), wide area network (WAN), the Internet, etc. A TMD 114 can communicate with the server 110 and the DCE 104 via a connection to the network 108. A client device 112 such as a smartphone, desktop computer, etc. communicates with the server 110 via the network 108. The server 110 can also utilize data such as maps from various data sources 116 (i.e., Google® Maps) and trained models via the network 108. The vehicle 102 can be, for example, an autonomous vehicle or a driver operated vehicle. The communication between the DCE 104 and the RFID tag 106, the DCE 104 and the server 110, the server 110 and the TMD 114, the server 110 and the client device 112, and the server 110 and the data sources 116 can be encrypted or unencrypted. The network 108 can be, for example, the Internet or a WLAN for an area. The server 110 can be a computing device local to the facility. The DCE 104 can be a reader device such as, for example, the TSL 1128 Handheld RAIN RFID reader made by IMPINJ™. One of ordinary skill in the art should appreciate that the server 110 can represent entities necessary for providing cloud computing such as infrastructure and service providers.

Figure 2:
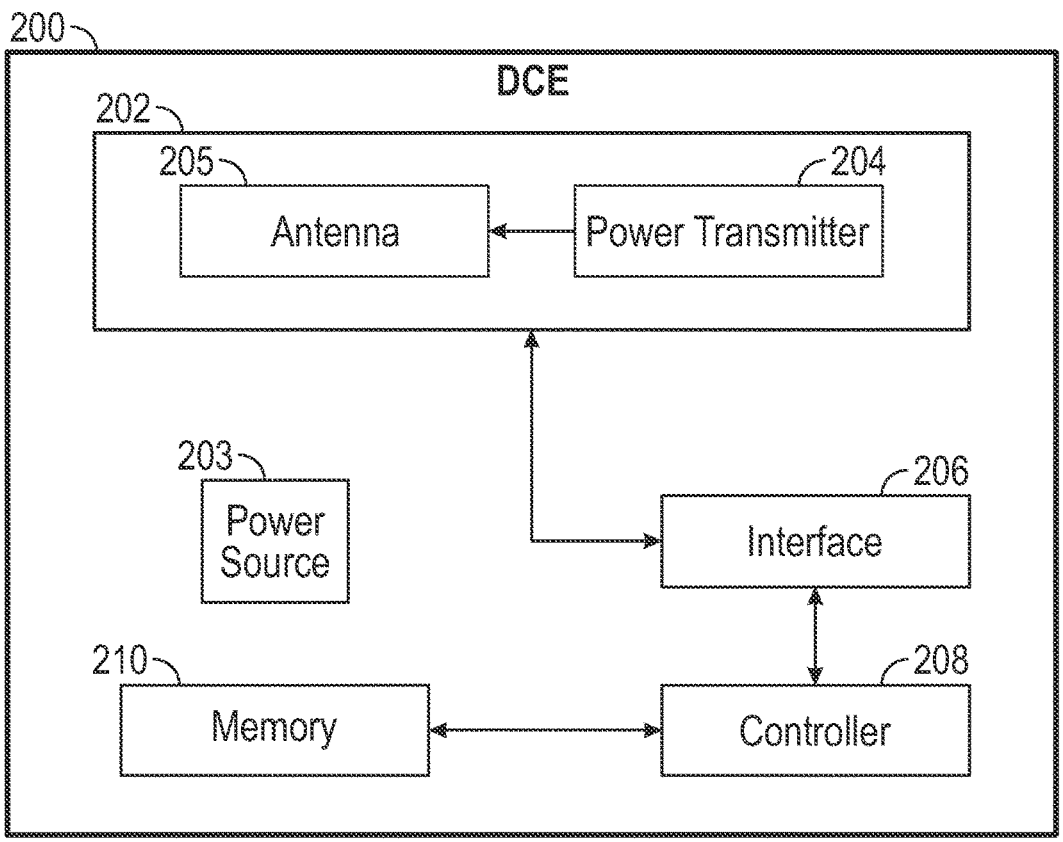
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of data and events received from RFID tags as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

Figure 3A:
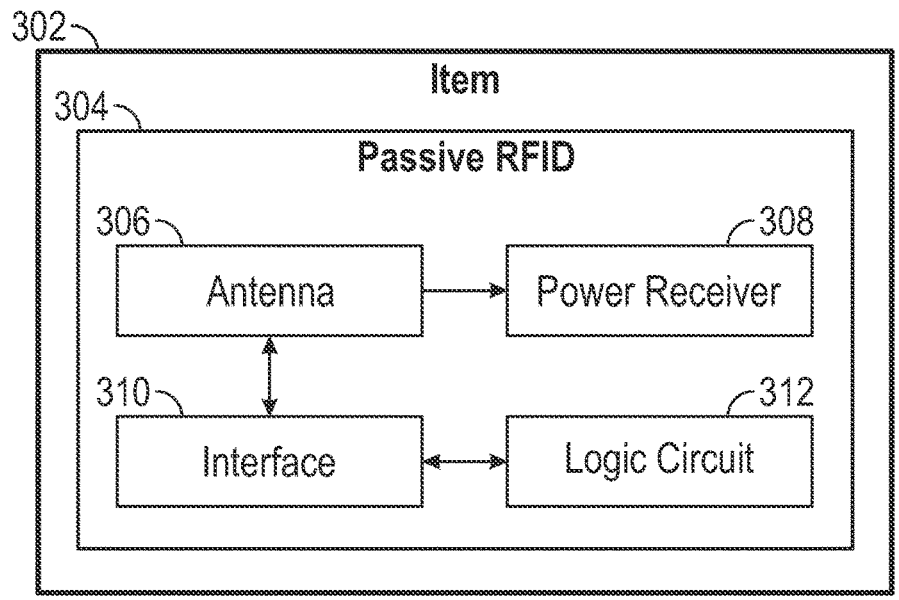
FIG. 3A is a block diagram illustrating exemplary portions of a passive-type RFID tag.

Referring to FIG. 3A, portions of an exemplary passive-type RFID tag 304 will be discussed. The RFID tag 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE 200. The power receiver 308 can include a power receiving coil for receiving power from the power transmission coil of the power transmitter 204 by electromagnetic coupling. The power receiver 308 can provide power to the chip 304 and/or charge a power source (not shown) such as a battery.

Generally, the logic circuit 312 generates data such as an identification of the RFID tag and/or the item to which it is affixed, state, location, and changes in any data or properties thereof over time, all of which will be referred to as item data. It should be noted that the item data includes situational data which refers to a) the identity of the RFID tag, the identity reference for a vehicle or individual identification to which the RFID tag is affixed, and b) the distance between an RFID tag and other RFID tags, the distance between the RFID tag and the DCE, the distance between the RFID and a client device such as smartphone, the identity and any identity references of the other RFID tags, DCEs and mobile client devices (i.e. smartphones) with which the RFID communicates, and any obtained from a sensor associated with i) the RFID tag or ii) another RFID tag, or client device (i.e. smartphone) with which the RFID communicates. Examples of the sensor data might be location in three dimensions, acceleration or velocity, displacement relative to some reference, temperature, pressure, to name a few.

The item data can also include data indicative of an event such as, for example, near field communication (NFC) established with the DCE or another RFID tag, a time duration for which the RFID tag 304 has been within a certain location, historical data, etc. Although not shown, the logic circuit 312 can include or be coupled to a non-volatile memory or other memory sources.

The interface 310 can format a received signal into an appropriate format for processing by the logic circuit 312 or can format the data received from the logic circuit 312 into an appropriate format for transmission. For example, the interface 310 can demodulate ASK signals or modulate data from the logic circuit 312 into ASK signals.

Figure 5A:
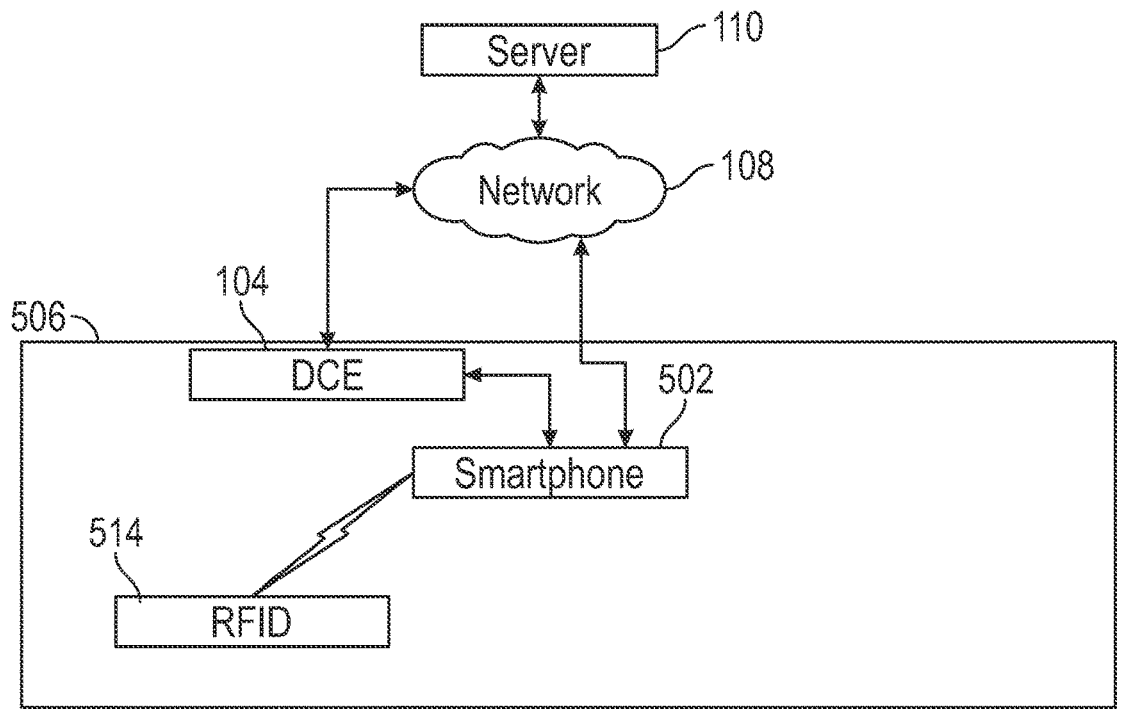
FIG. 5A illustrates an exemplary operating environment in which a smartphone acts as or together with the DCE to receive data from RFID tag associated with the item according to a modification to the first embodiment.
Figure 5B:
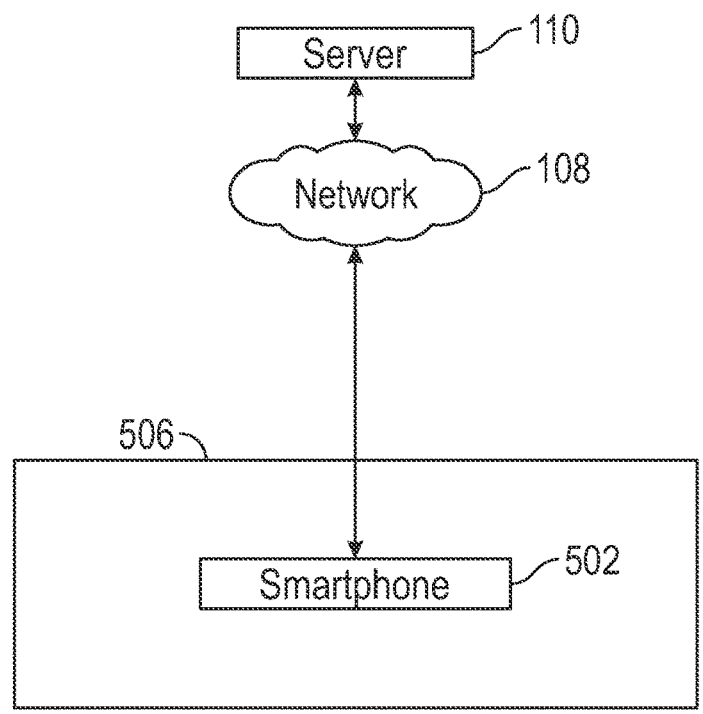
FIG. 5B illustrates an exemplary operating environment in which a smartphone replaces the DCE and the RFID tag associated with the item according to a modification to the first embodiment.

The DCE can also be or include a device reader such as the smartphone 502 shown in FIGS. 5A-5B or fixed gateway readers such as, for example, the XARRAY, XSPAN and XPORTAL made by IMPINJ™ or fixed and handheld readers such as the SPEEDWAY R420, SPEEDWAY R220, SPEEDWAY R120, ATID AB700 and TSL 1128 also made by IMPINJ™. The DCE can include chips such as the INDY series chip (INDY RS2000, INDY RS1000, INDY RS500, INDY R2000 or INDY R500, etc.) also made by IMPINJ™.

Figure 3B:
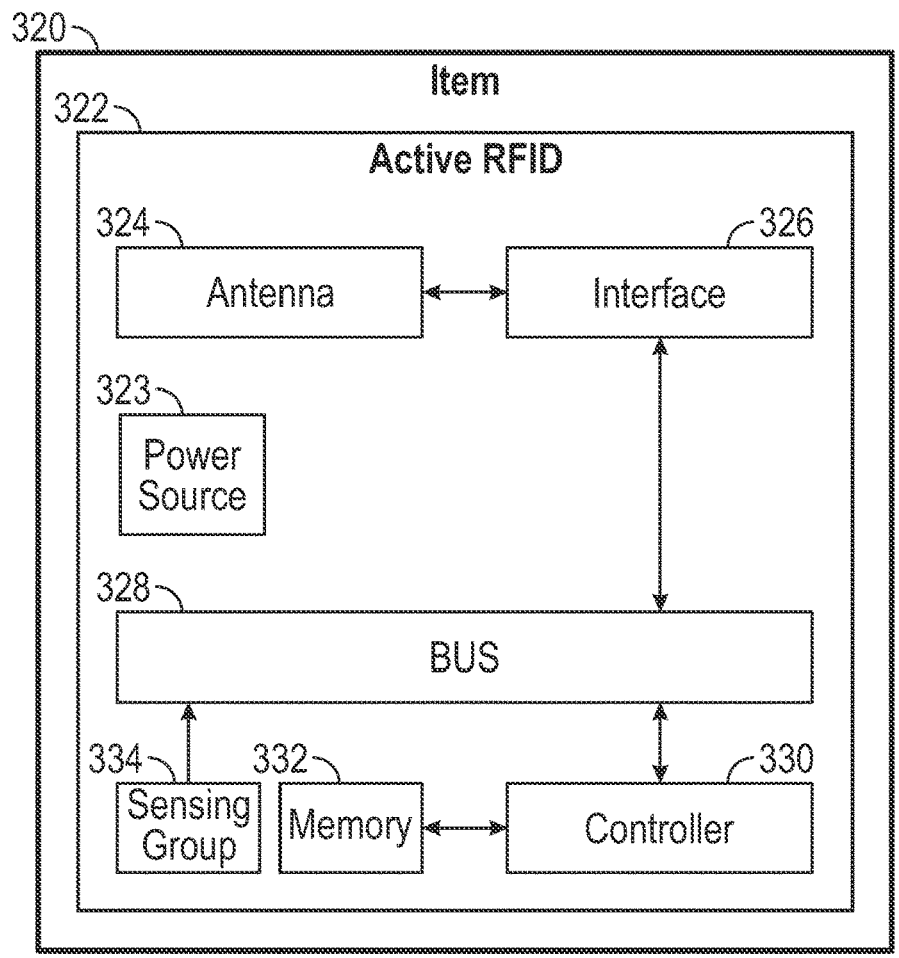
FIG. 3B is a block diagram illustrating exemplary portions of an active-type RFID tag.

Referring to FIG. 3B, circuit-level portions of the active-type RFID tag 322 on an item 320 will be discussed. The RFID tag 322 can include a power source 323, an antenna portion 324, an interface 326, a bus 328, a controller 330, a memory portion 332 and a sensing group 334. The power source 323 can be, for example, a battery. Although not shown, the tag 322 can also include a power management portion coupled to the power source 323.

The antenna portion 324 and interface 326 can be similar to those of the passive-type RFID tag 304. However, it should be noted that the antenna portion 324 can receive data from other passive-type and active-type RFID tags as well as the DCE and can send this and other data to the DCE, or other RFID tags.

The sensing group 334 includes sensing portions for sensing contact, motion characteristics such as an acceleration value, whether the chip is within a predetermined distance from another RFID tag, a distance from one or more other RFID tags and/or the DCE, and/or distance and angle from a baseline orientation. The sensing group 334 can include a set of accelerometers for determining the acceleration value of the item 320, a digital compass that collects orientation information about the item 322, a gyroscope for measuring angular rotation associated with the apparatus to provide an orientation value, a proximity sensor for detecting if the chip 322 is within a predetermined distance of another chip 322, a touch sensor layer and/or pressure sensor for sensing contact and magnitude of the pressure, and a geomagnetic sensor for sensing geomagnetic field strength. Preferably, the sensed motion characteristics include data represented in the time domain. The accelerometers can detect subtle movements along the three axial directions. The accelerometer reading, when combined with the data from the digital compass and/or the gyroscope, can facilitate motion detection. The sensing group 334 can include a separate OpenBeacon active tag or a Sense-a-Tag as described in "Proximity Detection with RFID: A Step Toward the Internet of Things" by Bolio et al., Pervasive Computing, IEEE, (Volume 14, Issue 2), published on April-June 2015, the contents of which are incorporated herein by reference. Further, in conjunction with or separately from the proximity sensor, the sensing group can include a distance sensor for measuring a distance to a target node such as another RFID chip. The distance sensor may be a received signal strength (RSS) indicator type sensor for measuring the RSS of a signal received from a target node such as the DCE or another RFID chip. The distance from the target node can be obtained by a plurality of RSS measurements.

The controller 330 is configured according to instructions in the memory 332 to generate messages to be sent to the DCE or another tag. Particularly, the controller 330 can be configured to send a registration message which includes identification data associated with the RFID tag 322 and thus the item 320. Further, in a case in which the RFID tag 322 wirelessly provides power to another passive-type RFID tag, the controller 330 can be configured to generate a message including identification data associated with the passive-type RFID tag, in combination with, or separately from its own identification data to the DCE.

The controller 330 can be configured to generate messages including data indicative of an event. These types of messages can be sent upon receiving a request from the DCE or another entity, upon occurrence of the event, or at regular intervals. Example events include near field communication established with another RFID tag, contact detected by the sensing group 334, positional information, a time duration of such contact and position, etc.

It should be noted that the passive-type RFID tag can also include a sensing group or be coupled to the sensing group. For example, the RFID tag 304 can be a Vortex passive RFID sensor tag which includes a LPS331AP pressure sensor. For example, the RFID chip 304 can be a MONZA X-8K DURA or X-2K DURA tag made by IMPINJ™ which include embedded sensors. Both active and passive types of sensors can include RSS measurement indicators. The controller or control logic can determine the distance from the RSS measurements based upon localization algorithms such as, for example, Centroid Location (CL), Weighted CL, or the Relative Span Exponentially Weighted Localization (REWL) algorithm as discussed in "Experimental Assessment of a RSS-based Localization Algorithm in Indoor Environment" by Pivato et al., IEEE Instrumentation and Measurement Technology Conference, published on May 2010, the contents of which are incorporated herein by reference. As mentioned above, the DCE 102 can store data regarding its fixed location (i.e. room 106). In this case, the physical location of the RFID tag 110 can be determined via the DCE 102. Alternatively, the RFID tags can obtain position from some external reference (i.e. a device with GPS or via a device that provides an indoor positioning system location reference, or WiFi hotspots, that themselves have a known location, which can somehow transmit WiFi ids to the RFID chips). This later approach, involving an external device other than the DCE 102, would occur via having the other external device communicate with the RFID tag and write location data to the RFID tag memory which is then sent along with any messages to the DCE. Further, the RFID tags could also be designed to record this location information from an external source upon being interrogated by a DCE.

Figure 9:
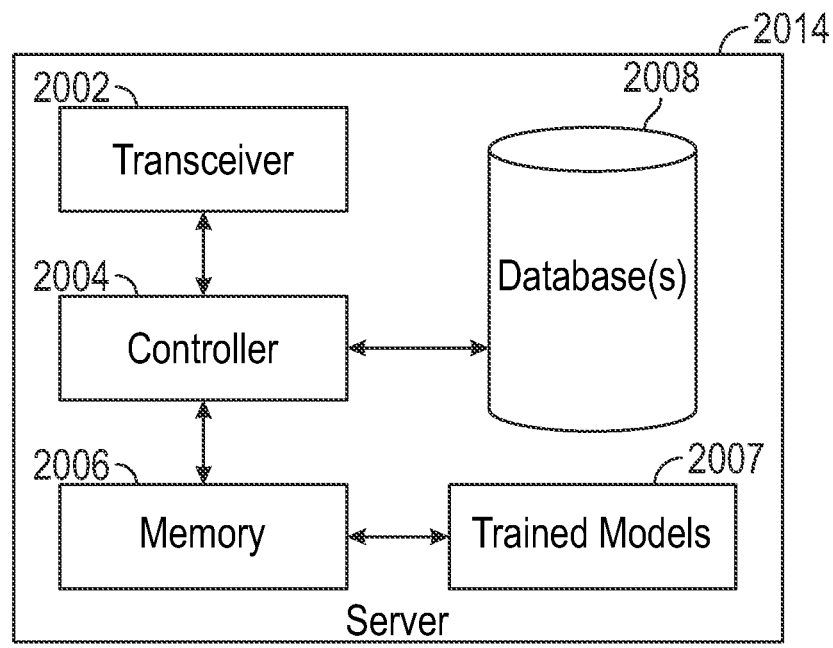
FIG. 9 is a block diagram illustrating exemplary portions of the server device.

Referring to FIG. 9, the server device 2014 includes a transceiver 2002, a controller 2004, a first memory portion 2006, a second memory portion 2007, and one or more databases stored in another memory source depicted generally by 2008.

The memory portions 2006, 2007, 2008 can be one or a combination of a variety of types of memory such as RAM, ROM, flash memory, DRAM or the like. The memory portion 2006 includes instructions for configuring the controller 2004. The second memory portion 2007 includes one or more trained models. It should be noted that the database and the trained models can be included in the memory portion 2006. They are shown separately here in order to facilitate discussion.

The databases 2008 can include, for example, vehicle identifications, vehicle driver identifications, drop-off requestor identifications, and usage attributes associated with each of the vehicle driver identifications and requestor identifications. The usage attributes can include a prior trip history and payment made/accepted of the vehicle/vehicle driver/requestor. The database 2008 can store attributes associated with each of the identifications such as average drive speed, rating history, etc.

The database 2008 can be, for example, an atomic data store. The transceiver 1102 receives data via the network from the DCE and resource requests such as, for example, http requests, via the network, from a client device. The resource request can include verification credentials such as a token issued from a certification authority and a user name and an information request for an information reply including usage parameters associated with one or more RFID chips. The transceiver 1102 sends the information reply including the usage parameters associated with the one or more RFID chips to the client device. The transceiver 1102 can be similar to the transceiver of the DCE.

The controller 2004 is configured according to the instructions in the memory 2004 to determine data in the database 2008 that is associated with the identification for each of the one or more RFID chips in the information request; generate an information reply including the usage parameters associated with the one or more RFID chips based upon the determined data; and store data in the message from the DCE in the database to be associated with the identification of the first RFID chip.

As will be discussed more fully below, the controller 2004 is further configured to store data related to an item such as tracking data in the database 2008 and further to predict an outcome associated with an event such as travel time or travel path based upon inputting attributes of the event into one or more trained models 2007 such as a neural network model or self-organizing map network and.

The controller 2004 and database 2008 can be configured to perform command query responsibility segregation in which commands are separated from queries to allow scaling of servers that respond to queries separately from servers delegated to responding to messages. The controller 2004 and database 2008 can further be configured to use event sourcing and/or event streaming to ensure all changes to an application state get stored as a series of events which can be not only queried but reconstructed.

It should be noted that in FIG. 1, one server was shown merely for ease of illustration. However, the server 114 may be a plurality of servers and databases connected to the network 112 via a load balancer and performing X, Y and Z axis scaling of the hardware and software.

Figure 10:
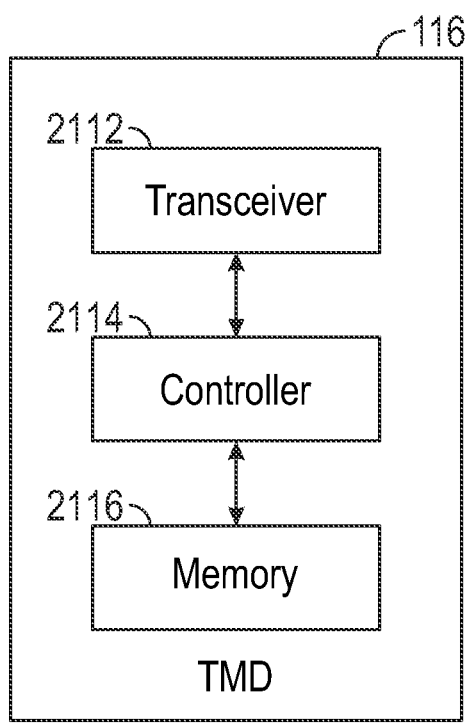
FIG. 10 is a block diagram illustrating exemplary portions of the TMD.

Referring to FIG. 10, the TMD 116 includes a transceiver 2112, a controller 2114 and memory 2116. The transceiver 2112 can be similar to the transceiver of the DCE. The transceiver 2112 receives information or resource requests such as, for example, http requests, via the network, from the client devices and other data storage sources. The resource request can include verification credentials such as a token issued from a certification authority (which must be determined to be valid and to contain the requisite claims for the resource being requested in order for the request to be successfully processed), and a user identifier and an information request for calculated quantifiable outcomes for a plurality of events. The transceiver 2112 sends an information reply to the client device. The controller 2114 is configured according to instructions in the memory 2116 to generate either solely visualization data (i.e. a json object) or graphical displays (i.e. html markup and javascript) including visualization data retrieved from server 2014 as the information reply that can then be used to generate a display on the client device. For example, the graphical display can indicate the deviation risk category or the predicted arrival time of each of a plurality of requested pick-up events as discussed later.

The server 110 and TMD 114 can be considered the backend devices of the system. The client devices of the system can be a desktop or fixed device, a mobile device, or another system (i.e. another backend server) that can run a native application or an application in a web browser. The various client devices contain a controller that executes instructions and a transceiver. The client devices can communicate with the backend system over the network 116 using a remote procedure call (RPC) or via Representational State Transfer (REST)-like or REST-ful architectural style or a messaging based architecture. The client devices communicate with the backend devices over Hypertext Transfer Protocol (HTTP), WebSockets, over another networking protocol encapsulated in Transmission Control Protocol (TCP), via message queues (for example Microsoft Message Queuing, Rabbit MQ, etc.) or any other protocols, for example, User Datagram Protocol, etc. The devices may also communicate via a cellular network (GSM, GPRS, CDMA, EV-DO, EDGE, UMTS, DECT, IS-136/TDMA, iDEN AMPS, etc.) or via other network types (i.e. Satellite phones). The data exchanged between the client devices and the backend device(s) can optionally be encrypted using Secure Sockets Layer (SSL), Transport Layer Security (TLS) and decrypted on the client device(s) and the backend device(s). The data may also be encrypted in transit using methods other than SSL/TLS (for example using a keyed-hash message authentication code in combination with a secret cryptographic key) and can be decrypted by the client or backend devices. SSL/TLS can alternatively be used in conjunction with one of the alternative encryption methodologies (belt-and-suspenders). Also, as mentioned, a client device may also consist of another third party back end system, such as another server that communicates with a database server.

Tracking Location of the Vehicle.

Figure 4:
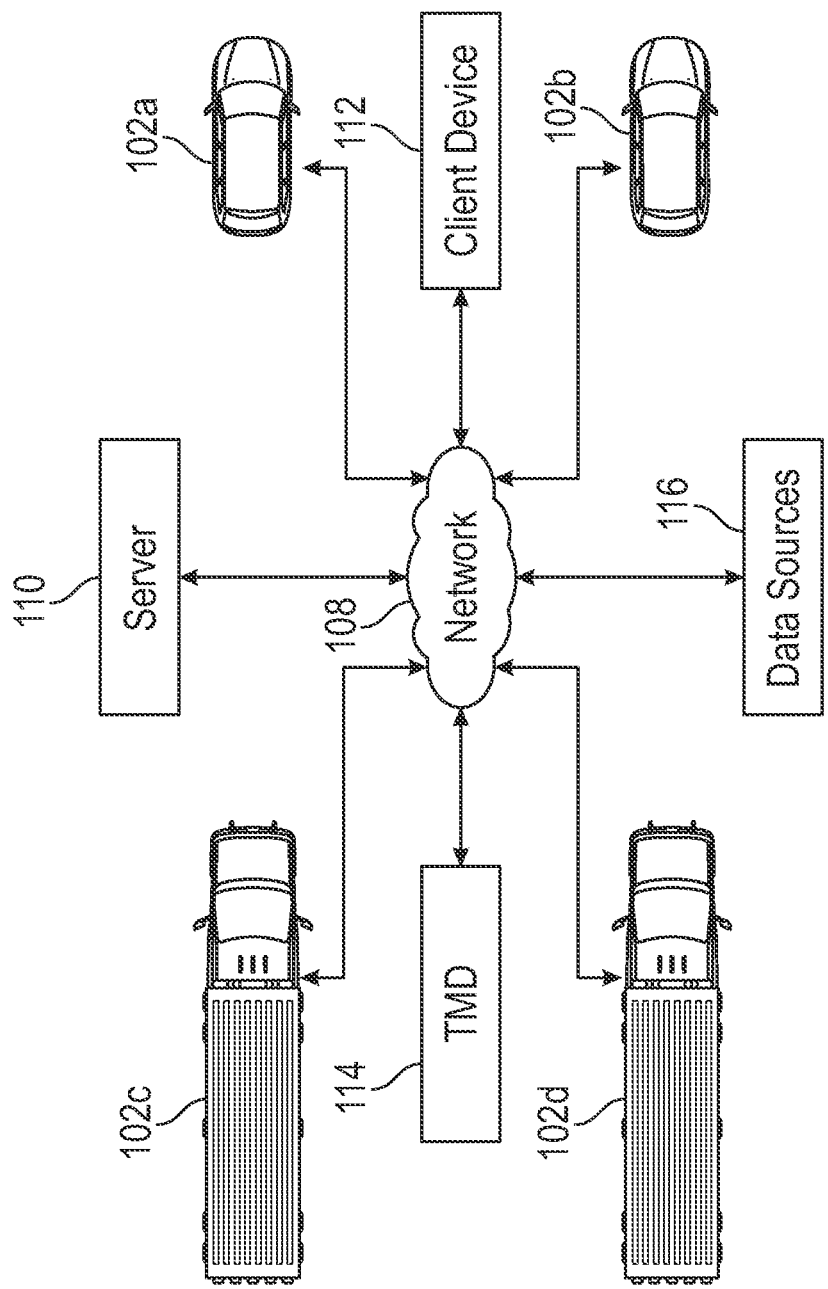
FIG. 4 illustrates an exemplary operating environment in which a plurality of vehicles exchange data with the server device according to a first embodiment.

FIG. 4 illustrates an exemplary case in which locations of a plurality of vehicles are tracked by the server 110 will be discussed. A client device 112 can send a pick-up request to the server via the network 110. The server device 110 can determine which vehicles 102a-102d are appropriate for the pick-up request. The vehicles can be passenger vehicles 102a-102b for picking up passengers or trucks 102c-102d for delivering materials. The server device 110 can utilize data such as maps in data sources 116 to determine travel paths for the vehicles. The TMD 114 can be used to provide an overall view of the system performance.

Each of the vehicles 102a-102d includes a tracking device. Returning to FIG. 1, the tracking device can be the DCE 103 and the RFID tag 106. Referring to FIG. 5A, an exemplary modification to the system will be discussed with respect to an exemplary operating environment in which a smartphone 502 communicates with the RFID tag 514. The smartphone 502 generates a broadcast message and receives messages indicative of events from the RFID tag 514 associated with item 506. The messages include registrations messages and events in reply to the broadcast message. The smartphone 502 can then send this data to the DCE 104 directly or via the network 108 or even directly to the server 110. For example, in areas in which there are no or very poor network service from the DCE 102, a mobile device such as the smartphone 502 can be used to augment or replace the network service. Referring to FIG. 5B, the smartphone 502 itself can be the tracking device. That is, the smartphone 502 can replace both the DCE and the RFID chip. In either case, the smartphone 502 can include a power transmitted for providing power (wireless or wired) to the RFID tag 514.

The smartphone 502 and/or the DCE 104 can be configured to locally persist and send the data to the server 110 either immediately upon collecting data or at a subsequent time after a batch of one or more pieces of data has been collected. The smartphone 502 and/or DCE 104 can purge the data sent from volatile or persistent memory immediately after successfully sending it or at a later time, either automatically or when prompted.

Figure 6:
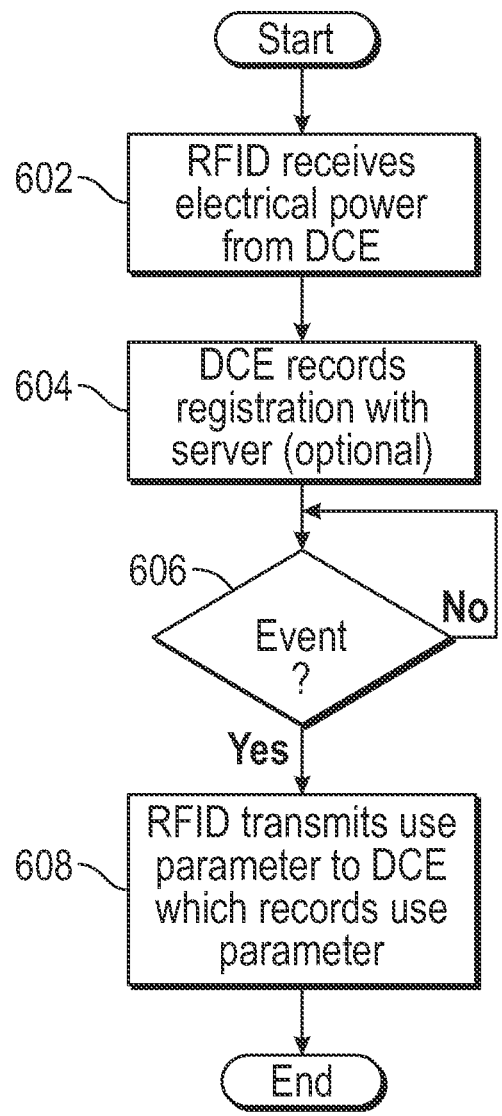
FIG. 6-8 are flow diagrams illustrating exemplary operations of the system according to an exemplary embodiment.
Figure 7:
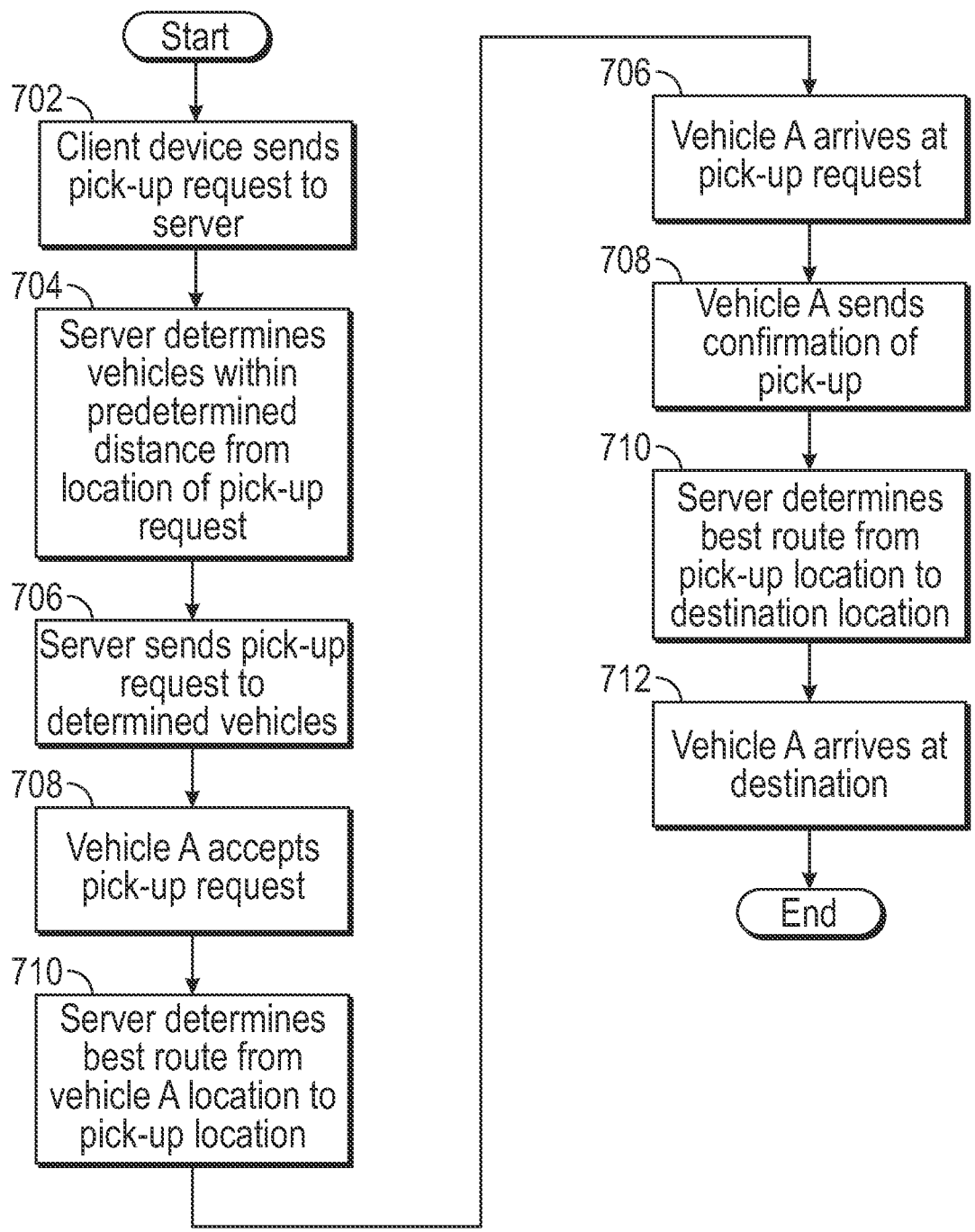
Figure 8:
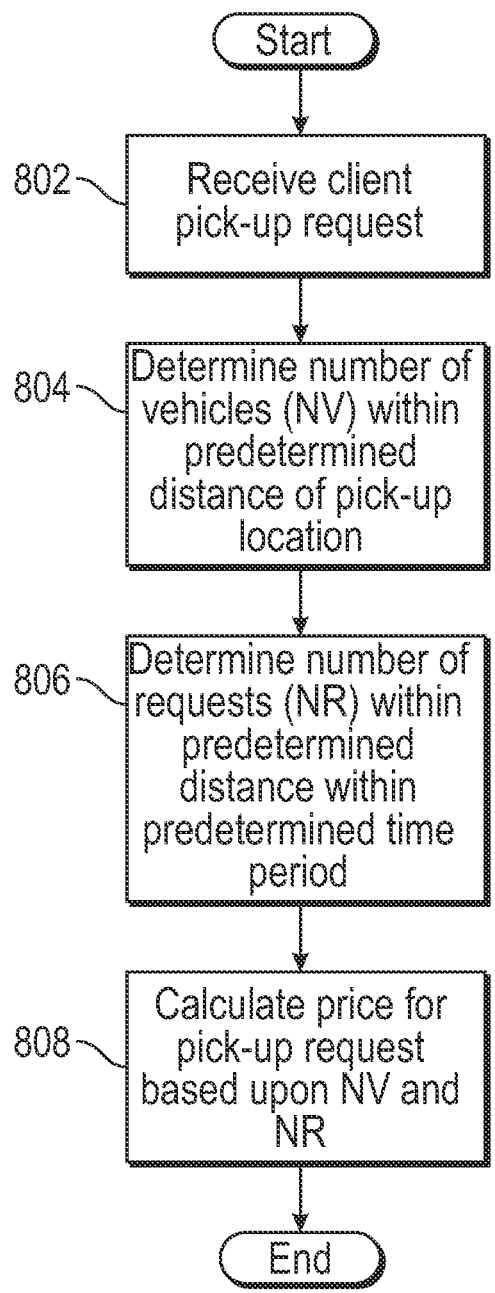

FIGS. 6-8 are flow diagrams illustrating exemplary operations of the system according to the first embodiment.

Referring to FIG. 6, the operations of the RFID chip and the DCE in a simple scenario will be discussed. At 602 a passive-type RFID chip receives electrical power wirelessly from the DCE. The wireless power can be sent along with a regular general broadcast message from the DCE or an interrogation request. Of course, if the RFID chip is active-type, this step can be omitted. At 604, the RFID chip sends registration information to the DCE, which records it in its memory. Particularly, the registration information can include the identification of the RFID chip. At 606, if the RFID chip and/or the DCE determines that an event has occurred, at 608 the RFID chip sends use parameters associated with the event to the DCE. The DCE records the usage parameters in its own memory or immediately transmits the information to the server to be stored in the database. The event can be, for example, merely the RFID chip receiving power from the DCE. Although not shown, the DCE can send messages indicative of this data to the server device.

Figure 11:
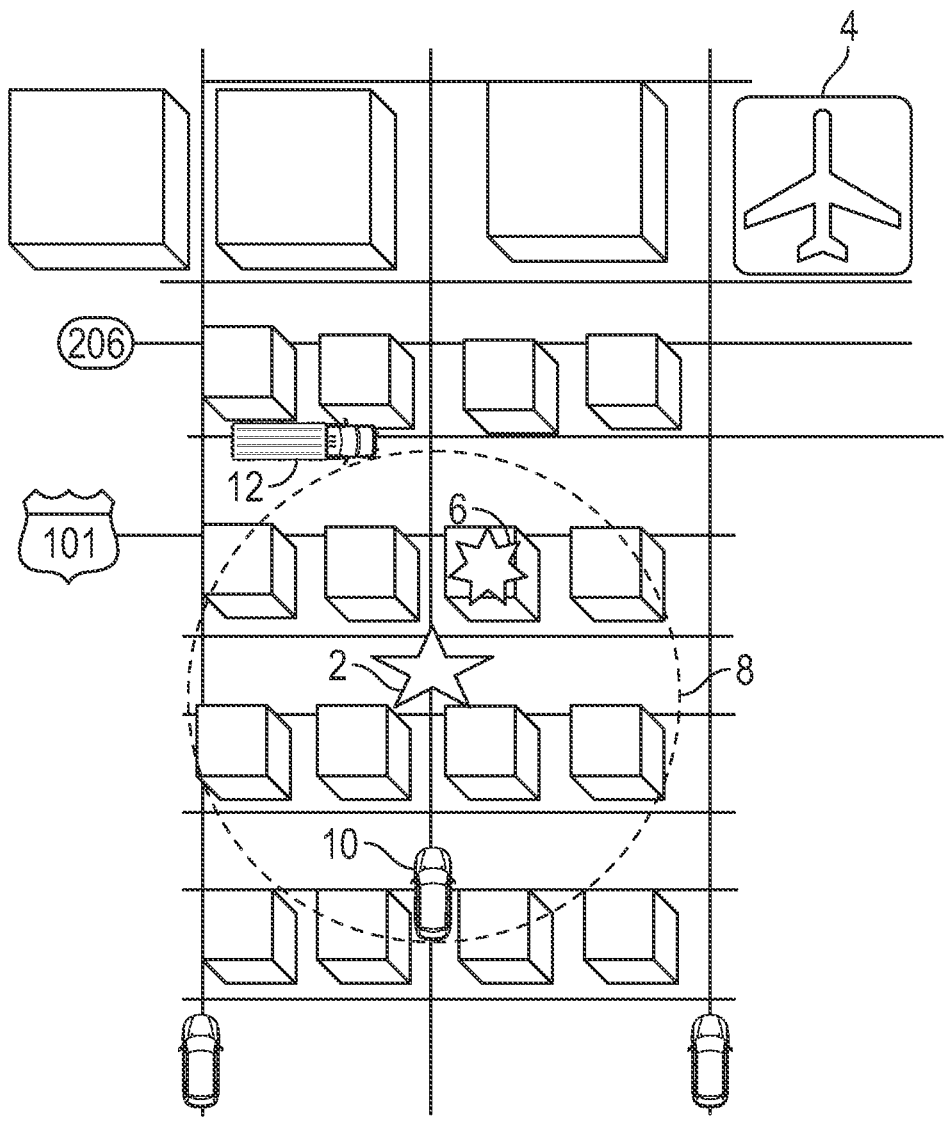
FIG. 11 illustrates an exemplary operating environment in which a client device makes a pick-up request and the server determines which vehicle(s) to send the pick-up request.

Referring to FIGS. 7 and 11, the operations of the system in a more complex scenario in which the vehicle receives a travel path for a pick-up request from the server will be discussed. At 702, the client device (request originator) sends a pick-up request to the server via the network. The pick-up request can include a pick-up location 2 and a drop-off location 4. Initially, the server device can confirm whether the pick-up location 2 is not appropriate for certain vehicles. For example, a truck 12 may not be able to stop at the requested pick-up location 2. Further, the requested pick-up location 2 may not be appropriate for any types of vehicles. In this case, the server device can send a message back to the client device requesting that the pick-up location be at a nearby pick-up location 6 appropriate for the vehicles.

After confirming the pick-up location 2, at 704 the server device 704 determines which vehicles are within a predetermined distance 8 from the pick-up location 2. In this example, the predetermined distance 8 is a radial distance from the pick-up location. The server device can cause the client device to send out a broadcast message that is only received by vehicles within the predetermined distance 8. Alternatively, the tracking devices in each of the vehicles can periodically send registration data including vehicle identification and location to the server device, which stores this data in its database. The server device can compare the pick-up location to the coordinates of all vehicles it is tracking to determine which of the vehicles are within the predetermined area.

At 706, the server device sends the pick-up request to the vehicle 10 determined to be within the predetermined area. In the case of driver operated vehicles, each of the vehicles can choose whether to accept the pick-up request. For example, the pick-up request can include a charge that will be credited to the vehicle. The driver may decide whether the accept the request based upon the charge. At 708, the vehicle 10 which is in the predetermined distance 8 accepts the request. It should be noted that in a case in which the vehicle is an autonomous vehicle, steps 706-708 can be omitted. That is, the server device can unilaterally decide which vehicle accepts the request. As discussed later, the server device can utilize trained models when determining the charge.

At 710, the server device determines a travel path from the current vehicle location to the pick-up location 2. The server device can access the map data from third party sources as discussed above. As discussed later, the server device can utilize trained models when determining the travel path. For a driver operated vehicle, the server device can send a message indicative of the travel path to the smartphone in the vehicle to be rendered on its display.

At 706, the vehicle arrives at the pick-up request location 2. At 708, the server receives a confirmation that the pick-up request has been fulfilled by a message from either the client device or tracking device or both.

At 710, the serve determines a best route from the pick-up location 2 to the drop-off location 4. Once again, here the server device can confirm that the drop-off location 4 is appropriate similarly to at 702. For example, the drop-off location 4 (in this example an airport) may have designated places for ride-share drop-offs and pick-ups. The server can store this information in its memory or obtain this information from third party data sources. For a driver operated vehicle, the server device can send a message indicative of the travel path to the smartphone in the vehicle to be rendered on its display.

At 712, the vehicle arrives at the drop-off destination 4. The server receives a confirmation that the trip has been completed from either the client device or tracking device or both. The server can store the trip parameters such as trip time and charge accepted by driver and request originator for future reference.

Returning to FIGS. 5A-5B, a mobile device such as smartphone 502 can serve as a proxy for identification of an individual rather than an RFID tag being on an identification. For example, the smartphone 502 can be configured to communicate with the server 114 and include NFC capability to communicate with RFID tags on, for example, a driver identification.

Referring to FIG. 8, the operations of the system in an exemplary scenario in which the server determines a price for the pick-up request will be discussed. At 802, the server receives the client pick-up request similarly to above. At 804, the server determines a number of vehicles NV within the predetermined distance from the pick-up request similarly to above. At 806, the server determines the number of pick-up requests NR that have been made within the predetermined distance within a predetermined time period.

At 808, the server calculates a price for the pick-up request based upon the NV and NR. Particularly, a higher price may be more appropriate when there is a high density of requests and a low density of available drivers (supply demand mismatch). Alternatively, a higher price can be offered in exchange for having a vehicle arrive at the pick-up request sooner.

Creating a Trained Neural Network Model to Predict an Outcome

Figures 12, 13:
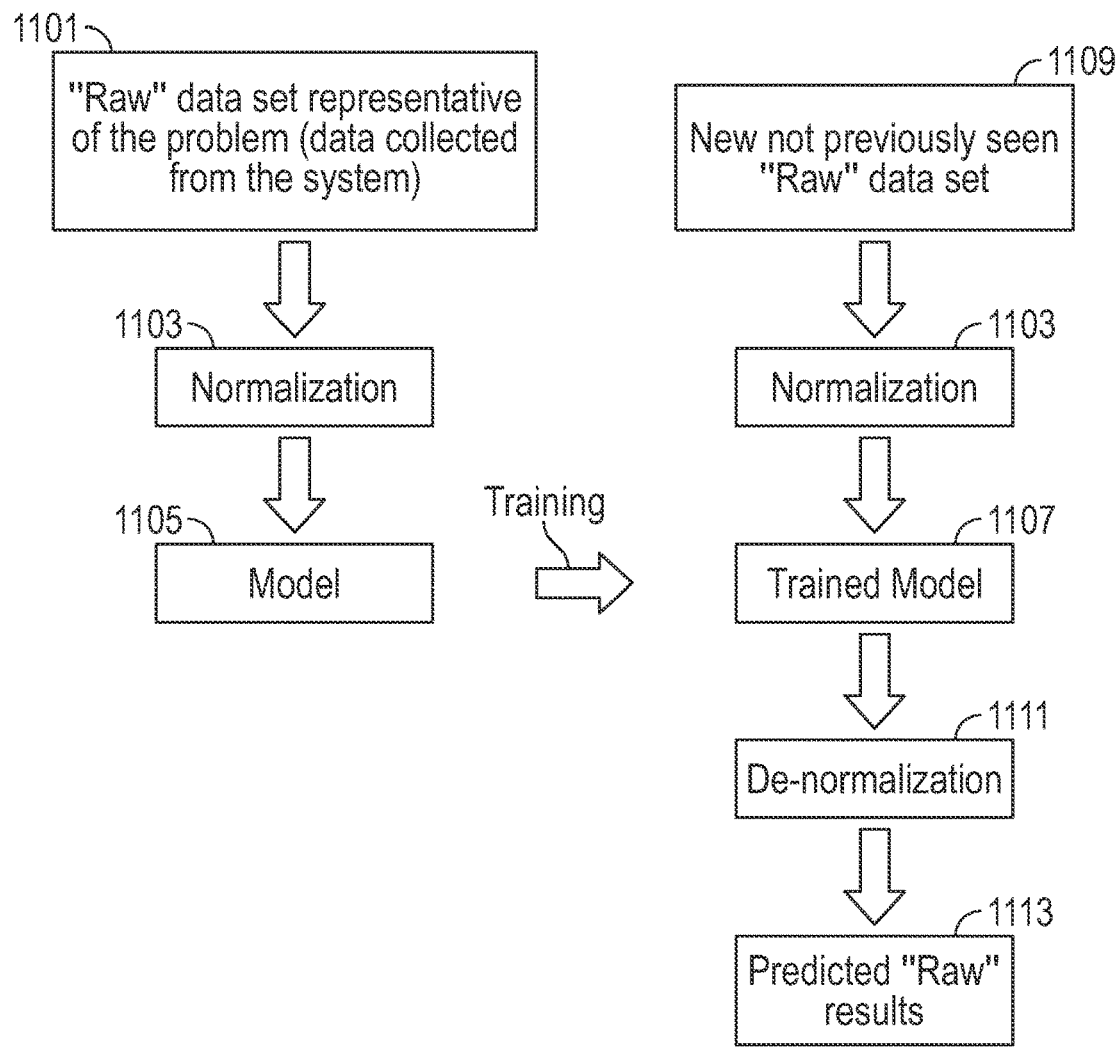
FIG. 12 is a block diagram illustrating high level operations for creating a trained neural network model (NNM) according to an embodiment.
FIG. 13 is an illustration of an exemplary data set for input attributes for various events.

Returning to FIG. 9, the server device 2014 stores one or more trained models 2007 which are used to determine an appropriate vehicle/driver, charge, travel path, and/or travel time for an event such as a pick-up request. A representation of the process for creating, training and using the trained model is shown in FIG. 12. Raw data 1101 is normalized 1103, and then input into the model 1105. The model 1105 is trained to form the trained model 1107. New data 1109 is normalized 1103 and input into the trained model 1107. The output data of the trained model 1107 is de-normalized 1111 to obtain the output data (predicted raw results) 1113. As shown in FIG. 13, the raw data 1101 and new data 1109 include sets of data [1, 2 . . . N] with known outcomes and properties of each of the data. For example, the data can be past pick-up request events with known deviation outcomes. The properties of the data can be attributes of the vehicle, origination location of the pick-up request or vehicle, drop-off location, time, date, driver identification, etc.

The model 1105 is trained by an iterative machine learning algorithm. After initial deployment, the server 2014 will also continuously collect data from a variety of sources along with actual related system operational outcomes; this data can subsequently be used as training data. As such, the TMD/server is able to continuously learn and improve its ability to predict the outcomes of interest. In addition, the knowledge of the system can continue to evolve in the event the system dynamics change. Take, for example, the travel time from the request pick-up location to the drop-off location. There is a relationship between the multitude of attribute data the system collects and the outcome in question. Although there are various attributes the server 2014 can collect about a vehicle, there is no one specific mathematical relationship or equation that describes the relationship between these exemplary attributes of the vehicle and the outcome of interest. However, because of the server's machine learning capabilities, it has the ability to "learn" or be trained from pre-existing data and from the data it collects prospectively. Said another way, the server 114 "learns" from experience.

Data Set Encoding, Normalization and De-Normalization

Neural network models only use numerical values for training and processing. Thus, any nominal categorical data fields that are a part of raw data that will ultimately be used by models in the system are first encoded to numerical values and "raw" numerical data in many cases by a preprocessing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

Figure 14A:
FIGS. 14A-14B are illustrations of various exemplary approaches for normalizing the data set.

An example of one of the independent predictors (input x-data) or input attributes that can be utilized by the system is the number of vehicles available for a pick-up request. Suppose there are 19 available vehicle and that this "raw data" value needs to be normalized to a −1 to 1 normalization range. If the actual range of the possible number of transitions is 0 to 50, for example, then to normalize this input x-data, the system's continuous or numeric normalization process would carry out normalization calculations similar to those illustrated herein. Initially, the value can be plotted on an actual range as shown in FIG. 14A. Then a normalization calculation can be carried out as shown below:

$$\{[(19-0.0)*(1.0-(-1.0))]/(50.0-0.0)\}+(-1.0)=-0.24$$

Figure 14B:
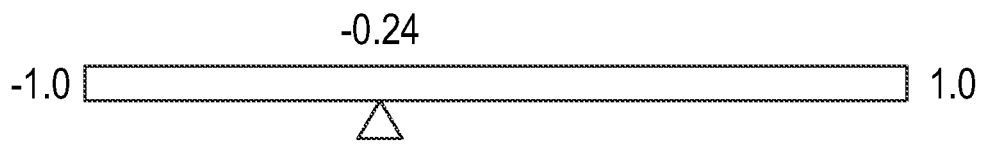

Referring to FIG. 14B, equivalent value plotted on a normalization scale is shown.

Figure 15A:
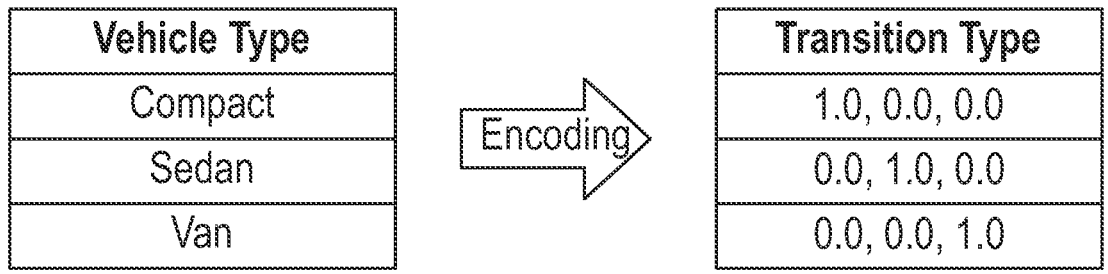
FIG. 15A-15B are illustrations of various exemplary approaches for encoding the normalized data set.

In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 15A. For example, one of the attributes that may be used is the vehicle type. In this case of three vehicle types: compact vehicle, sedan and van. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is a first transition type {0.0, 0.0, 1.0} but the ideal (real) value is actually a second different transition type {0.0, 1.0, 0.0}, it is apparent that there is only error in two parts. Said another way, if the predicted and the ideal (real) values are compared, the first value is 0.0 in both (i.e. is correct), while the other two values are both wrong. This is unequal distribution of errors.

Figure 15B:
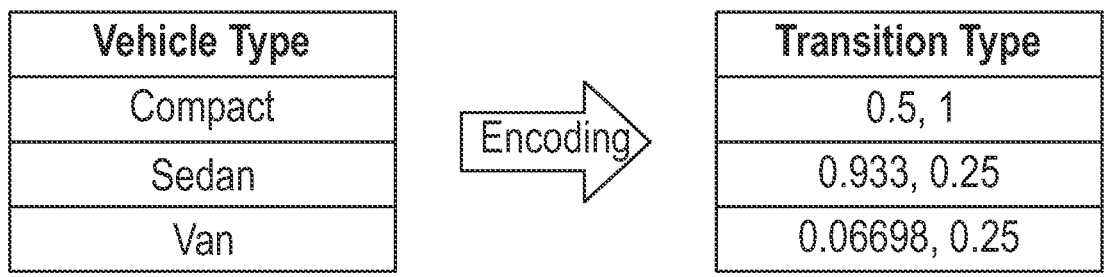

Due to this shortcoming of one-of-N encoding, particularly in instances when there are more than two nominal categories, the server can employ equilateral encoding (one-of-(N−1) encoding shown in FIG. 15B or one-of-(C−1) dummy encoding for encoding nominal categorical data. When equilateral encoding is used, fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$distance = \sqrt{\frac{(i_1 - a_1)^2 + (i_2 - a_2)^2 + \ldots + (i_n - a_n)^2}{n}}$$

Where the variables represent the following:

i=ideal (real) output value a=actual (predicted) output value n=number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:

$$=((0.5-0.933)^2+(1.0-0.25)^2)^{1/2}$$

$$=(-0.433^2+0.75^2)^{1/2}$$

$$=(0.187489+0.5625)^{1/2}$$

$$=(0.749989)^{1/2}$$

$$=0.8660$$

Ideal: {0.06698, 0.25}
Actual: {0.5, 1}
Euclidean Distance:

$$=((0.06698-0.5)^2+(0.25-1)^2)^{1/2}$$

$$=(-0.43302^2+(-0.75^2)^{1/2}$$

$$=(0.1875063204+0.5625)^{1/2}$$

$$=(0.7500063204)^{1/2}$$

$$=0.8660$$

Equilateral encoding is not employed by the system in scenarios where there are less than three distinct nominal categories.

Exemplary embodiments of a supervised and unsupervised neural network training algorithm used to create a trained model will be discussed. However, these embodiments are merely examples. Those skilled in the art know any variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others. While the exemplary embodiments herein do not detail every machine learning approach employed by the system to solve the technical problem, this should not be construed as an omission of these capabilities or approaches which the system can and in some cases does leverage to solve the technical problem.

There are three primary categories of machine learning tasks: classification, regression and clustering tasks.

Classification

Figure 28A:
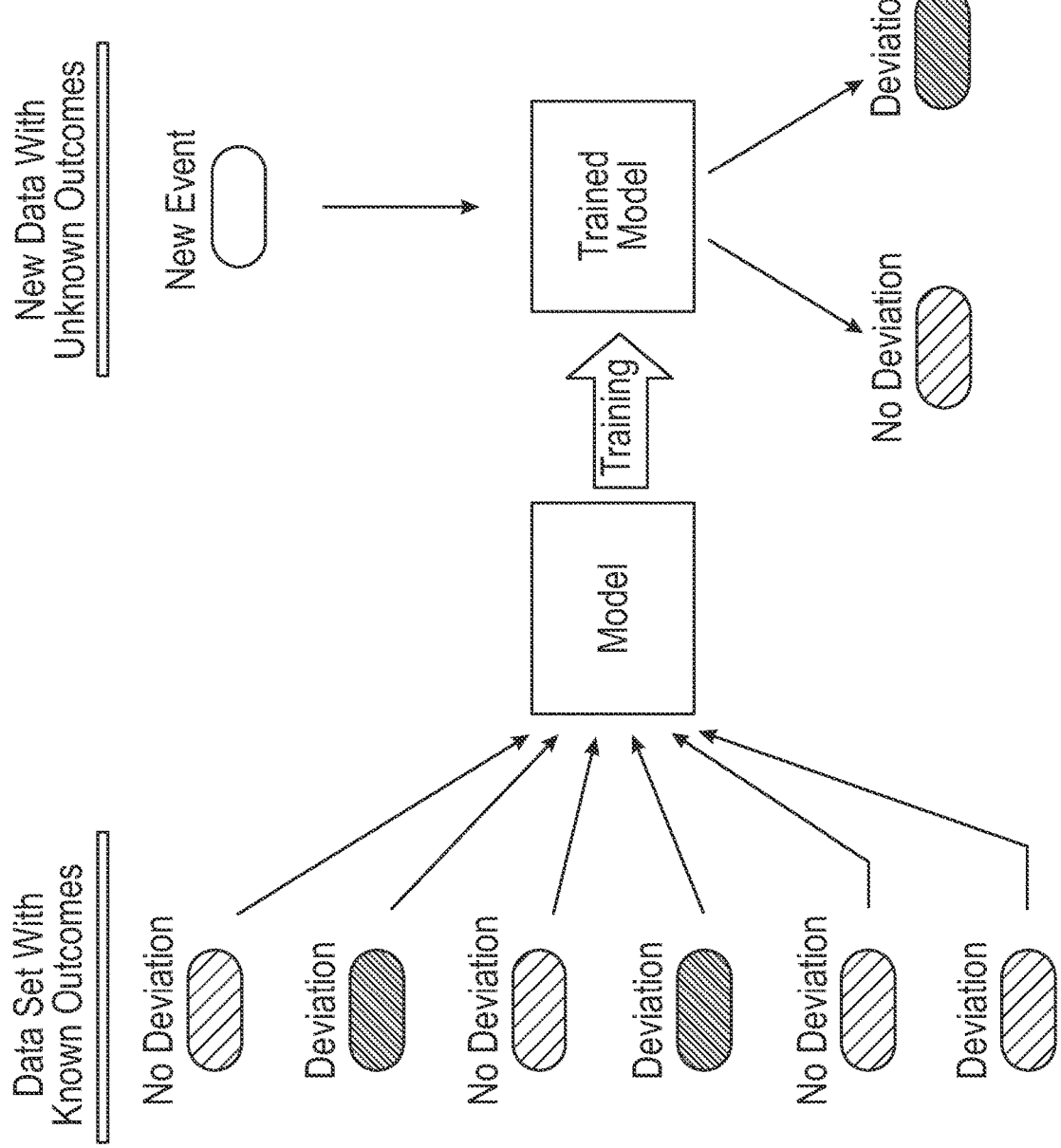
FIGS. 28A-28B are illustrations of a case in which the model is used to categorize the deviation risk of a plurality of travel paths.
Figure 28B:
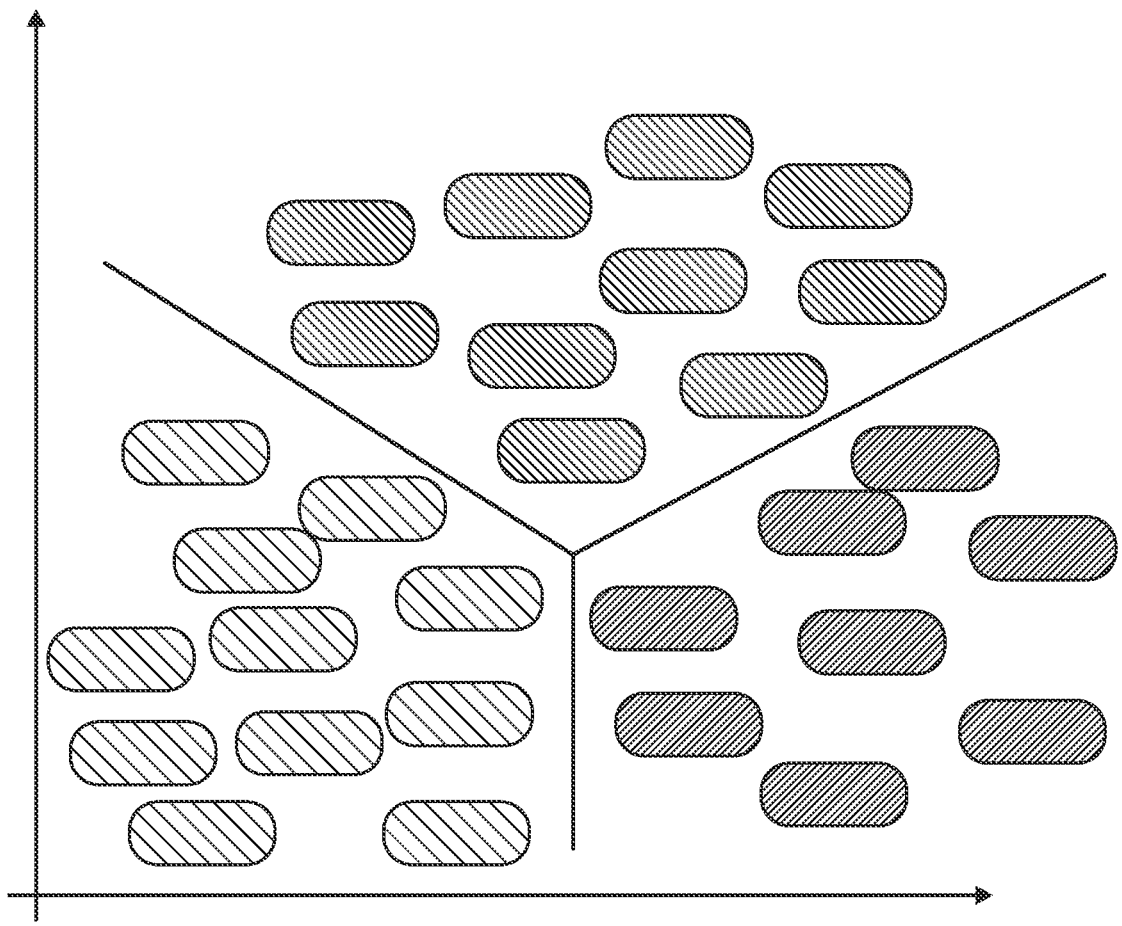

Referring to FIGS. 28A-28B, a classification task for predicting deviation risks (travel time delay) of a pick-up request is shown. The machine learning task entails a two-step supervised learning process which utilizes both input and output data in the model training process. Model construction is done using a representative training data set and the model, once trained is used for classifying new or unseen cases, for example a pick-up request at risk of deviation—predicts nominal categorical assessment or assignment. The inputs are collected vehicle data attributes/properties. The output will be predicted categorical risk for deviation, no deviation, moderately deviated and severely deviated. As shown in FIG. 28B, like events can be clustered together to reveal non-obvious related deviations (or causes thereof) such as, for example, a similar cause (a particular street, or traversing a particular path, all on a particular time, or or some other characteristic).

Regression

Figure 29:
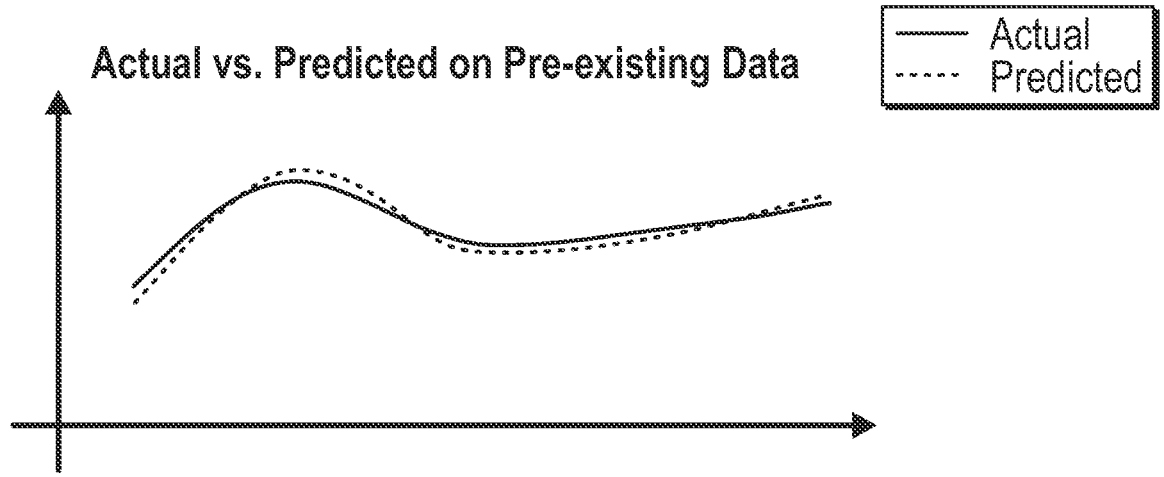
FIG. 29 is an illustration of exemplary regression tasks performed by the TMD.
Figure 29:
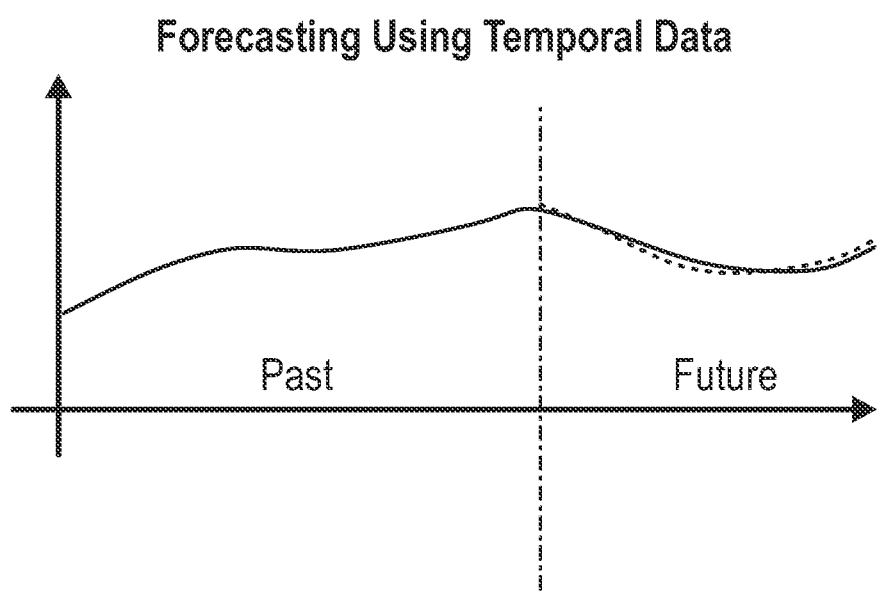

Referring to FIG. 29, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of deviation (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 2014 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boost model performance and efficiency for some tasks.

Another exemplary task, for which the server 2014 uses unsupervised learning, as detailed further later herein, is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 16:
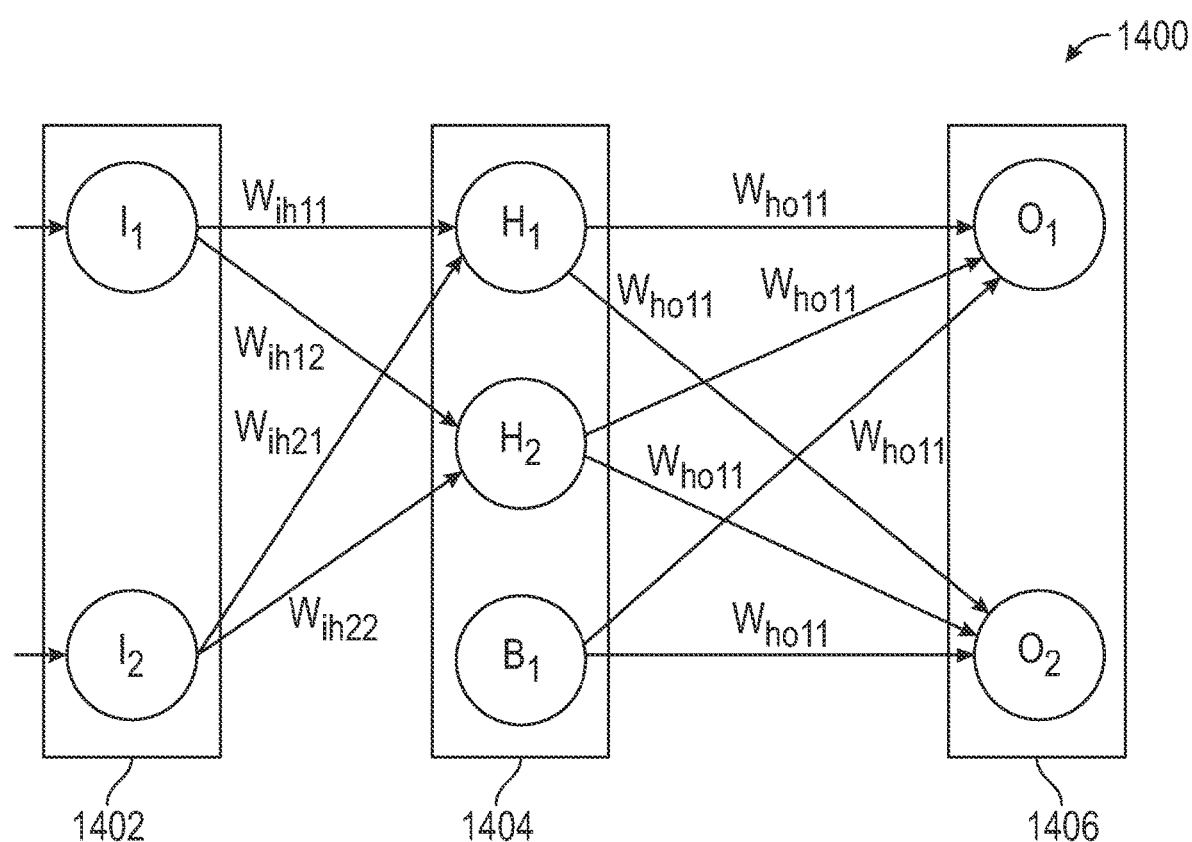
FIG. 16 is an illustration of an exemplary simple feed forward NNM.

Referring to FIG. 16, the backend devices can use a neural network model (NNM) 1400. The NNM 1400 includes an input layer 1402, a hidden layer 1404 and an output layer 1406. The input layer 1402 includes input neurons ($I_1$ and $I_2$) which provide input signals to the network without any processing units (processing units, described further herein are comprised of summation and activation functions). The hidden layer 1404 includes hidden neurons ($H_1$ and $H_2$) which provide a means to converge the network's solution leveraging additional processing units (summation and activation functions). At times, if these neurons are not present, the neural network may not be able to output the desired result. The hidden layer 1404 can also include bias neurons (Bi) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $I_1$ and $H_2$ has a synaptic weight of $w_{ih\ 12}$. The $w_{ih\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus, the notation $w_{ih\ 12}$ not only denotes the neurons that are connected or involved but also the direction of the connection.

Figure 17:
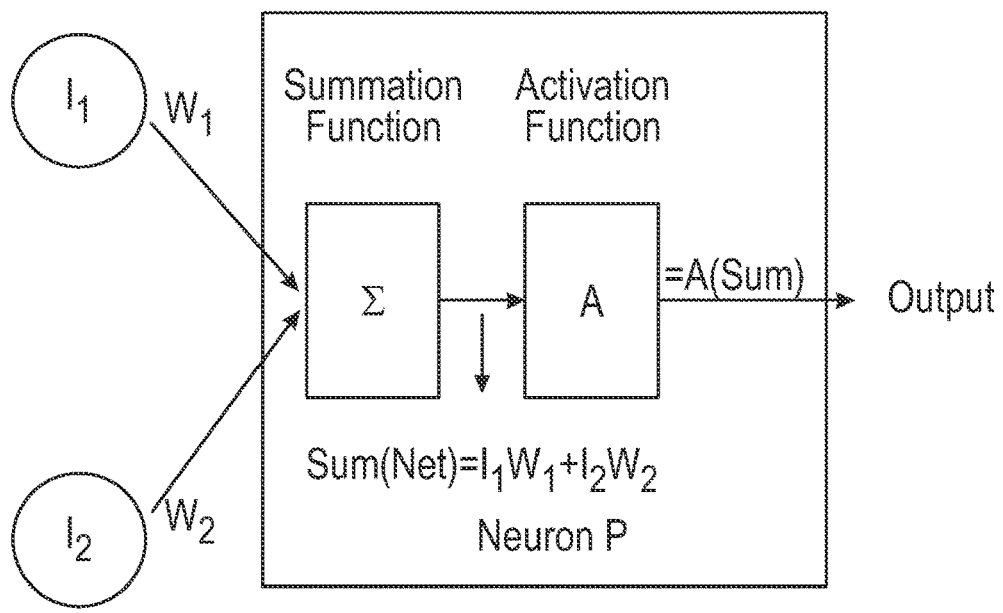
FIG. 17 is an illustration of an exemplary neuron of the NNM.

As shown in FIG. 17, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The Sigmoid Function $$f(x) = \frac{1}{1 + e^{-x}}$$

Figure 18A:
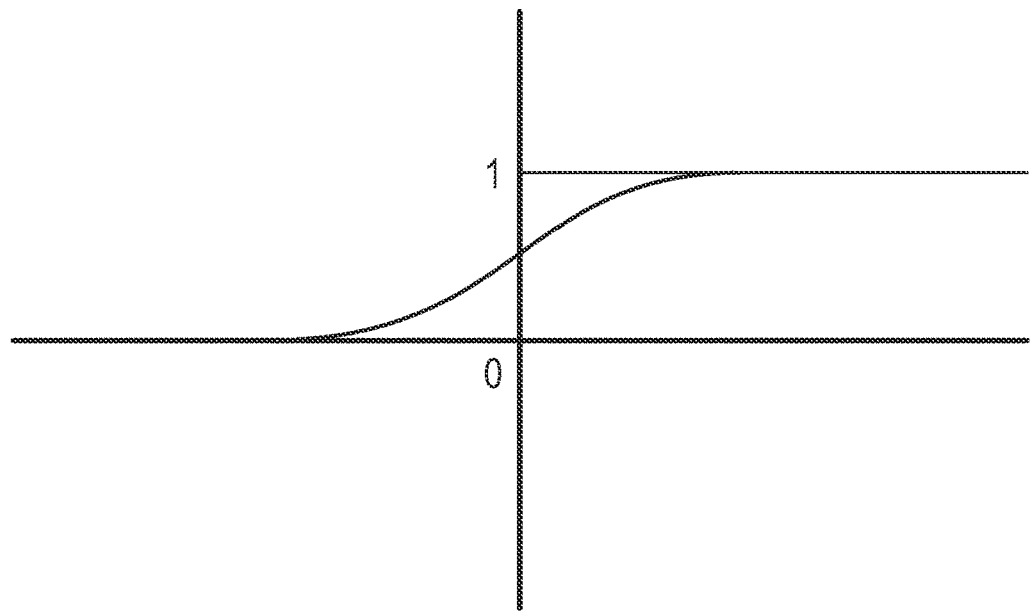
FIGS. 18A-18C are illustrations of exemplary activation functions for the neurons of the NNM.

As shown in FIG. 18A, a characteristic of the sigmoid function is that for all values on the x axis, the function output value (y axis) will lie between 0 and 1. The sigmoid function is used in instances where only positive outputs are expected.

The Hyperbolic Tangent Function $$f(x) = \frac{e^{2x} - 1}{e^{2x} + 1}$$

Figure 18B:
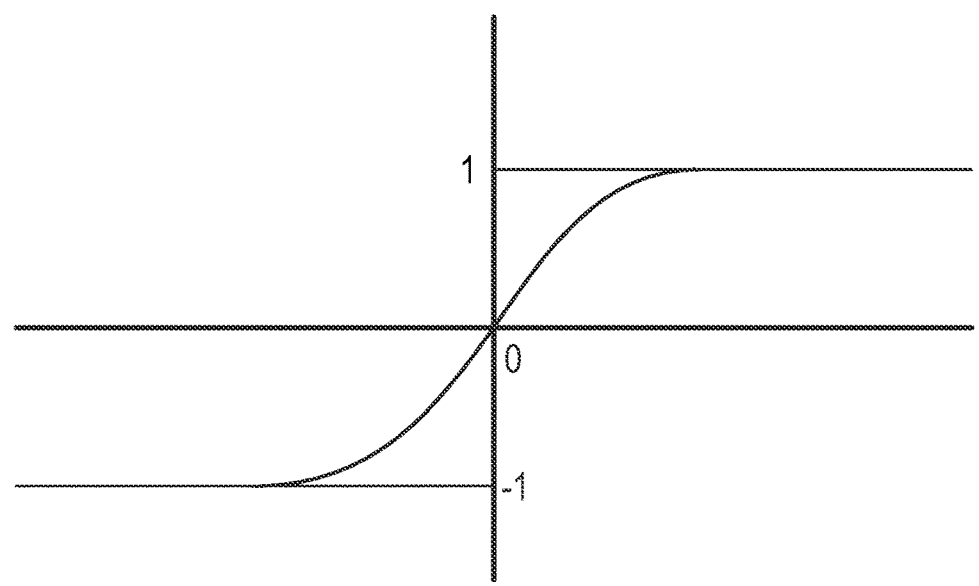

As shown in FIG. 18B, a characteristic of the hyperbolic tangent function is that for all values on the x axis, the function output (y axis) will lie between −1 and 1. The hyperbolic tangent function is used by the system in instances when both positive and negative outputs are expected.

The Linear Function $$f(x) = x$$

Figure 18C:
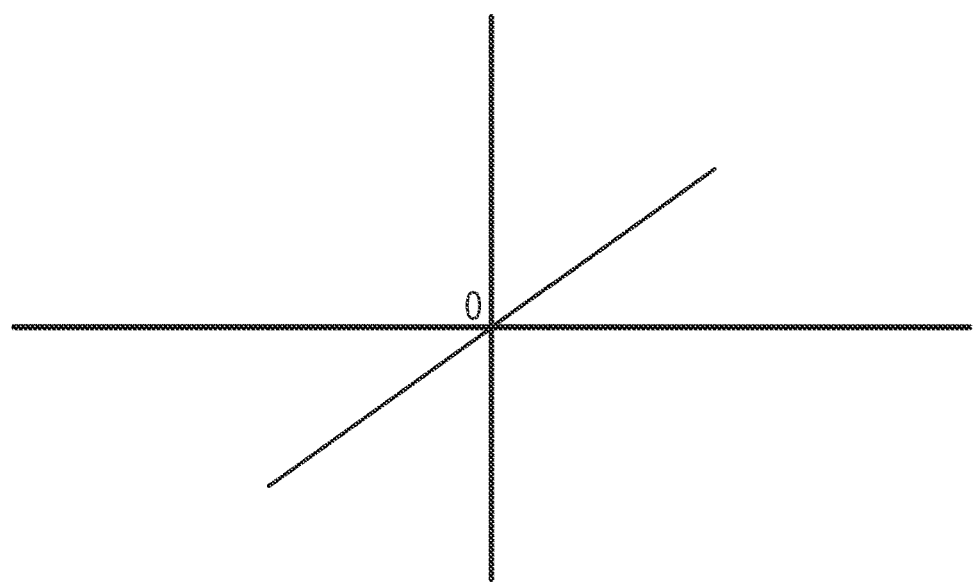

As shown in FIG. 18C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the server 2014 employs a plurality of activation functions to accomplish its objectives.

Figure 19:
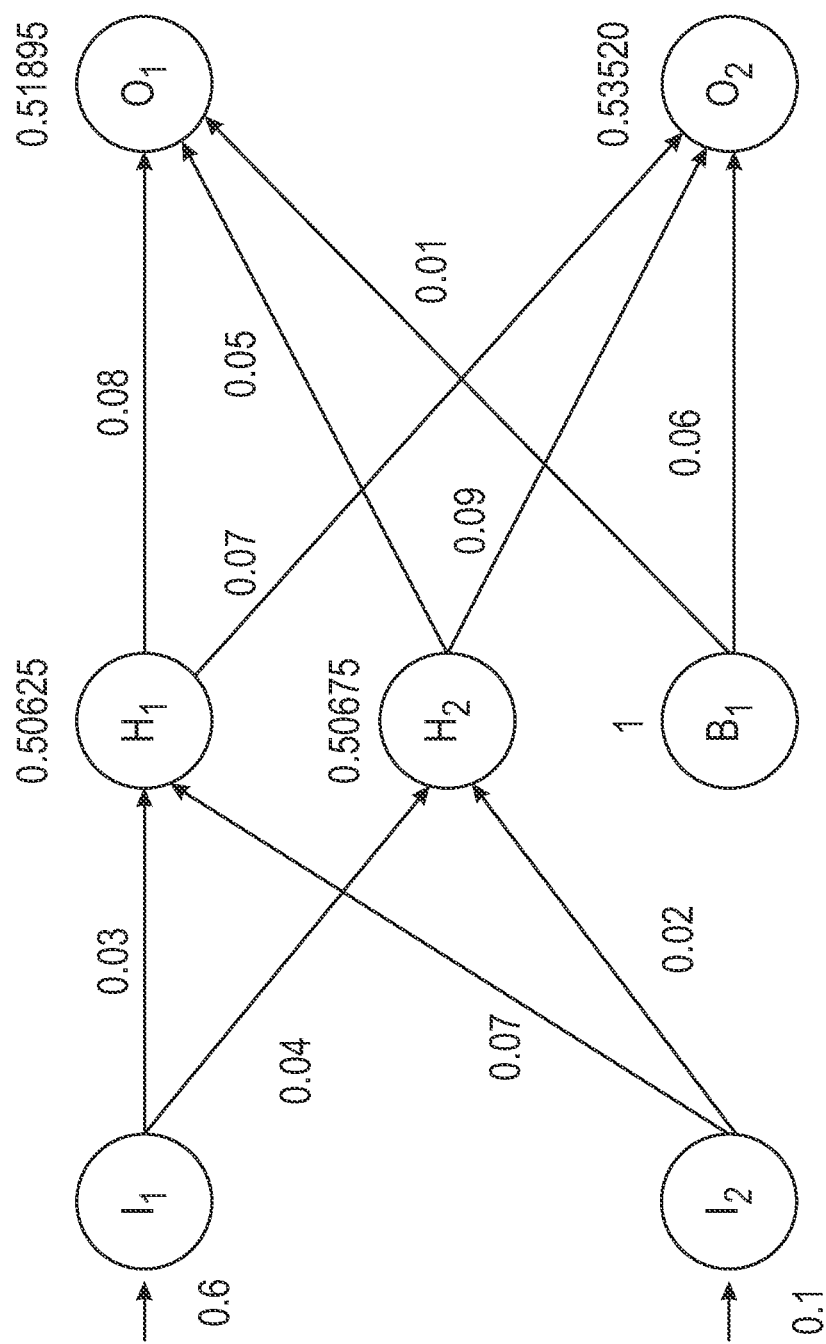
FIG. 19 is an illustration of exemplary computations of the NNM.

A NNM is a neural network architecture with a particular structure tailored to a particular problem statement. An exemplary problem statement the server's 2014 neural networks model is the prediction of whether a travel path from a pick-up location to a drop-off location will cause delay. Using a trained NNM, the server 2014 predicts the likely outcome using a plurality of the properties or attributes of the vehicle (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 19 is demonstrative of a feed forward structure, however other possible neural network structures or architectures include, but are not limited to ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self-Organizing Map (Kohonen), among others. Feedback networks, for example Elman and Jordan Networks, are at times leveraged by the system particularly in instances where the sequence of events (order of data) is material. Each neuron of the neural network model also has a defined activation function. Each neuron may have more than one activation function in different layers. In the exemplary neural network of FIG. 19, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 19. This calculation process is used during each model training iteration and subsequently when the trained model is used to make predictions from previously unseen input data:

$H_1$ $\text{Sum} = 0.6 * 0.03 + 0.1 * 0.07$ $= 0.018 + 0.007$ $= 0.025$ $\text{Output} = A(\text{Sum}) = 0.50625$ $H_2$ $\text{Sum} = 0.6 * 0.04 + 0.1 * 0.02$ $= 0.024 + 0.002$ $= 0.027$ $\text{Output} = A(\text{Sum}) = 0.50675$ $O_1$ $\text{Sum} = 0.50625 * 0.08 + 0.50675 * 0.05 + * 0.01$ $= 0.0405 + 0.0253375 + 0.01$ $= 0.0758375$ $\text{Output} = A(\text{Sum}) = 0.51895$ $O_2$ $\text{Sum} = 0.50625 * 0.07 + 0.50675 * 0.09 + * 0.06$ $= 0.0354375 + 0.0456075 + 0.06$ $= 0.141045$ $\text{Output} = A(\text{Sum}) = 0.53520$ During the training process, the synaptic weights are adjusted to minimize the error of the output. Thus, the final synaptic weights of the trained model are only known once model training is complete. After successful training of the model, the finalized synaptic weights are then used to make predictions.

Training the NNM

The server 2014 applies machine learning algorithms to modify the synaptic weights of each model's connections as it learns the patterns in the data. Thus, trained models in the system are system models with finalized synaptic weights that result in the most minimal error. Training algorithms along with representative data sets presented to each of the models for the purpose of training are employed by the system to update the synaptic weights of each model's connections with values that minimize the error.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\sum_n E^2}{n}$$

The mean square error (MSE) is the sum the square of all local errors divided by the total number of cases.

Sum of Square Errors (ESS)

$$\frac{\sum_n E^2}{2}$$

The sum of square errors (ESS) is the sum of the square of all local errors divided by two (2).

Root Mean Square Error (RMS)

$$\sqrt{\frac{\sum_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 20:
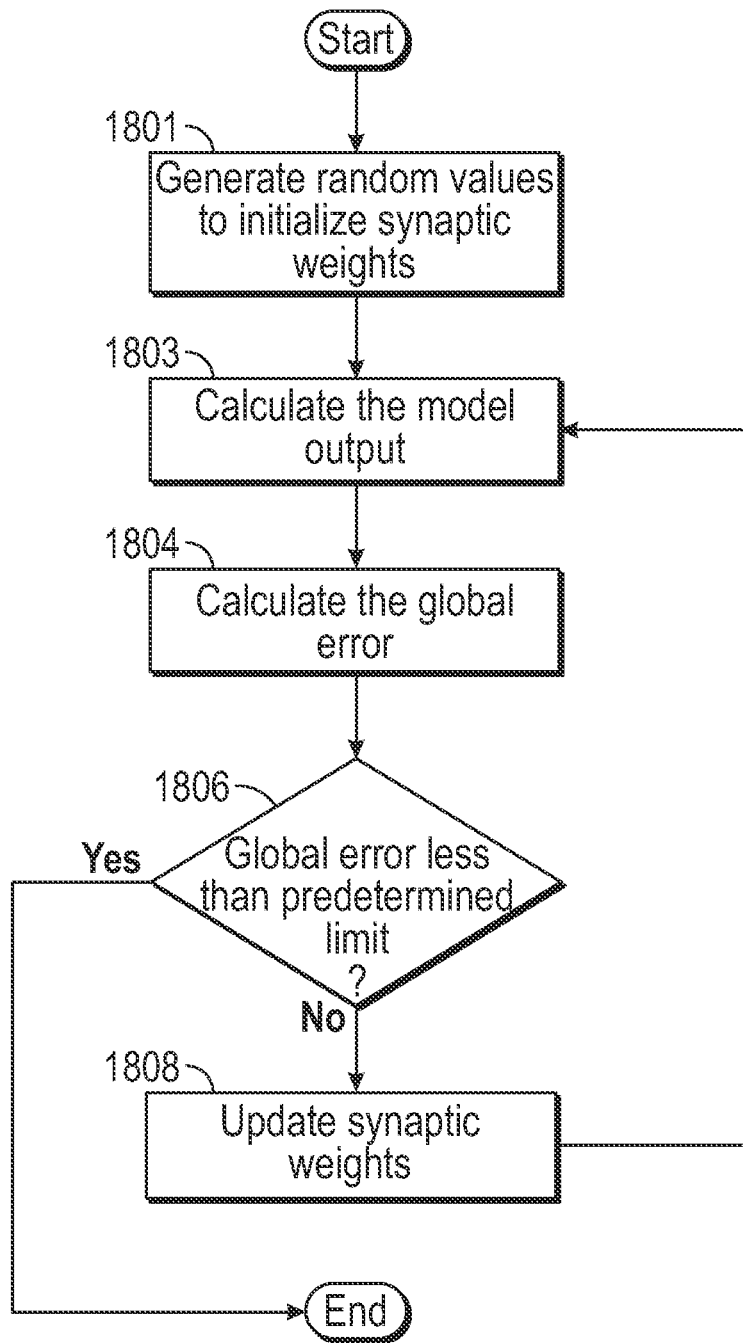
FIG. 20 is a flow diagram illustrating exemplary operations of the system for training the NNM.

Referring to FIG. 20, the approach for training the NNM based upon training data will be discussed. The training data is quantifiable outcomes (deviation or no deviation, deviation probability) of a plurality of past pick-up request events and attributes of each of the past events. Initially, at 1801, values of the plurality of synaptic weights are assigned to random values. At 1803, the output values of the model are calculated for the current "row" or case in the training data being used for the current training iteration (i.e. "row" being the one event or case used for the current training iteration out of the available events in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another event from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 21:
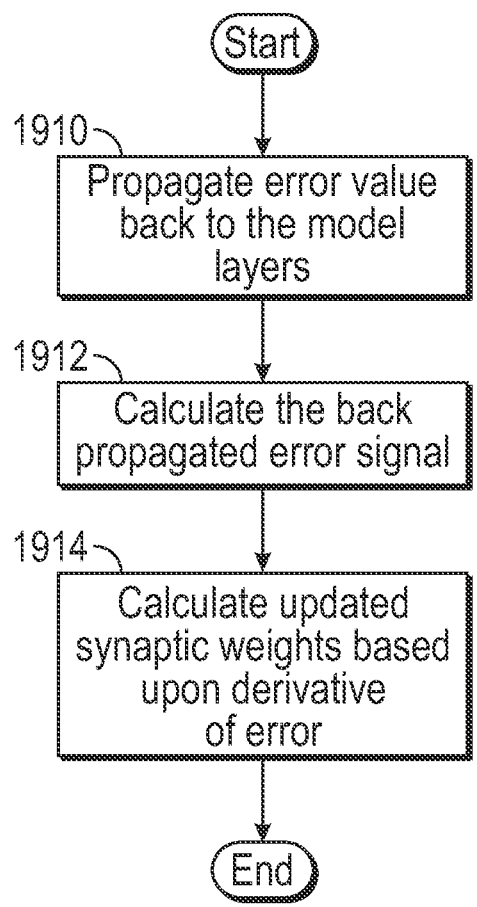
FIG. 21 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 21, a gradient-decent procedure can be used to update the synaptic weights on each training iteration. At 1910, the error value is propagated to the model layers. The gradient-decent procedure is used to determine the direction of change of the synaptic weight(s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

Figure 22:
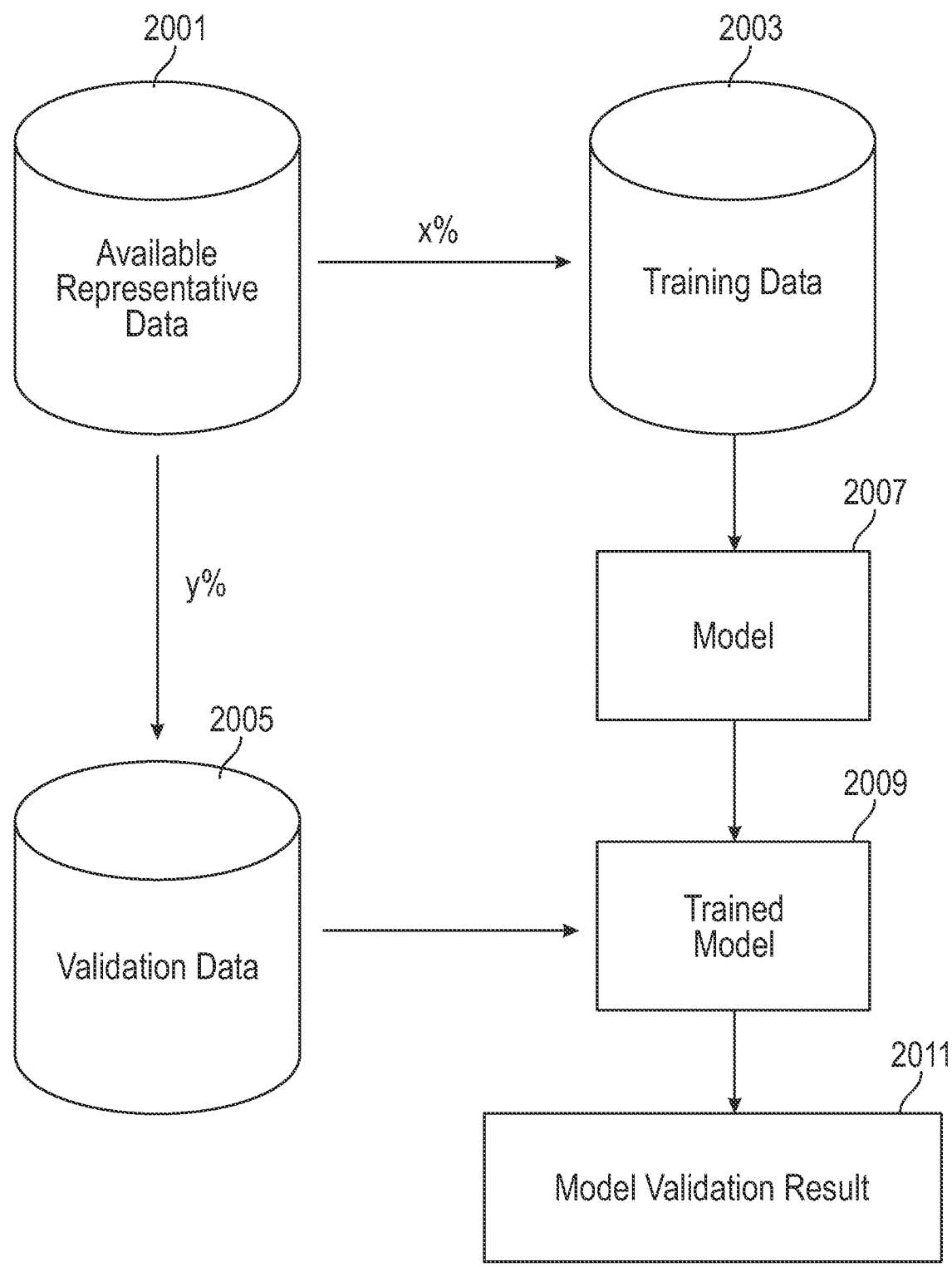
FIG. 22 is block diagram illustrating high level operations of the process for training the NNM and validating the trained NNM.

The training process for the NNM employs a representative data set, which can be a plurality of past events as discussed above. Referring to FIG. 22, the cases in the representative data set 2001 are divided into two unique data sets by some ratio or percent x allocated to the training data set 2003 and percent y allocated to the validation data set 2005. The ratio of cases allocated to the training data set 2003 versus those allocated to the validation data set 2005 varies. Before the allocation of cases to the training data set 2003 or the validation data set 2005, an optional step of data shuffling can be carried out by the system to help ensure all types of data in the representative data set 2001 gets distributed to both the training 2003 and the validation 2005 data sets. The training data set 2003 was used to train the NNM 2009 as discussed above. The validation data set 2005 can be used to validate the trained NNM 2009 because the real outcome of each case in the validation data set is known. The server can generate an output value (model validation result) 2011 of the trained NNM 2009 for each past event of the validation data set 2005, wherein each of the output values 2011 represents a calculated quantifiable outcome of the respective pick-up request event. Then the server can determine if the output values 2011 correspond to the quantifiable outcome within the predetermined global error.

The training data set 2003 along with the defined system models, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2009 is then used to predict the outcome for cases in the validation data set 2005, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

Returning to FIG. 16, the backend device receives a plurality of input attributes of a new pick-up request event. This data may come from a client device, from the database at the server, or a combination. The data is pre-processed (for example, normalized) to generate an input data set, and the data is input into the trained model 1107 which then generates an output value. The output value is then post-processed (for example, de-normalized). Finally, the output value is classified into a deviation risk category (classification task) or a value such as the probability of deviation or the predicted duration of deviation (regression task) to predict the outcome. For example, in the simplest case the de-normalized output value can be a Boolean value (deviation or no deviation). In another case, the output value can be a probability of deviation occurring. In this case, the TMD or server may assign probability ranges which define particular delay categories. In another case, the output value can be a calculated deviation time (predicted duration of deviation). In this case, the TMD or server may assign time ranges to define particular deviation categories.

Unsupervised Learning

Figure 23A:
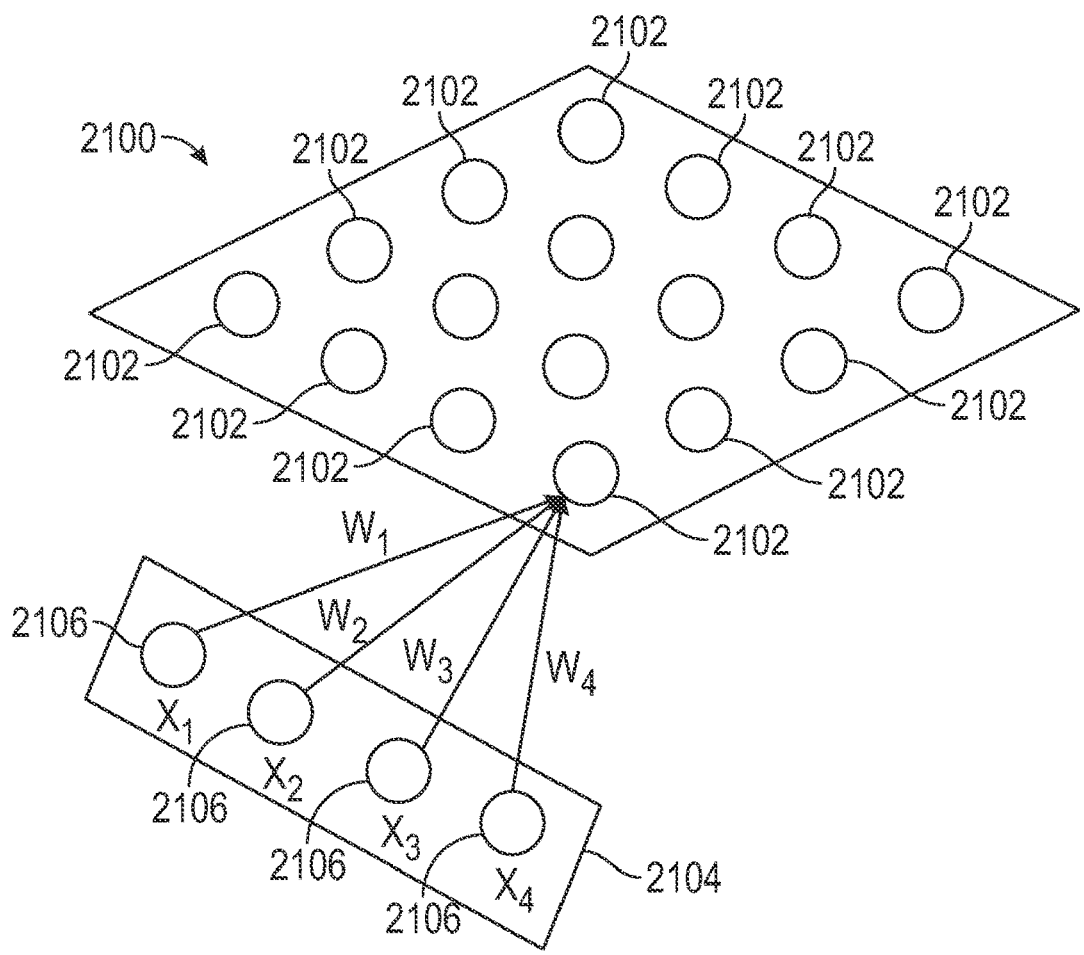
FIGS. 23A-23B is an illustration of an exemplary Self-Organizing Map (SOM) and the input data set to the SOM network.
Figure 23B:
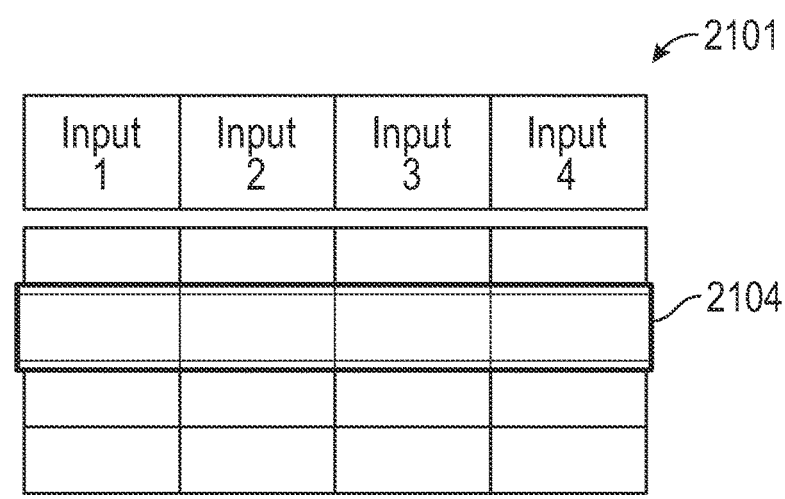
Figure 23C:
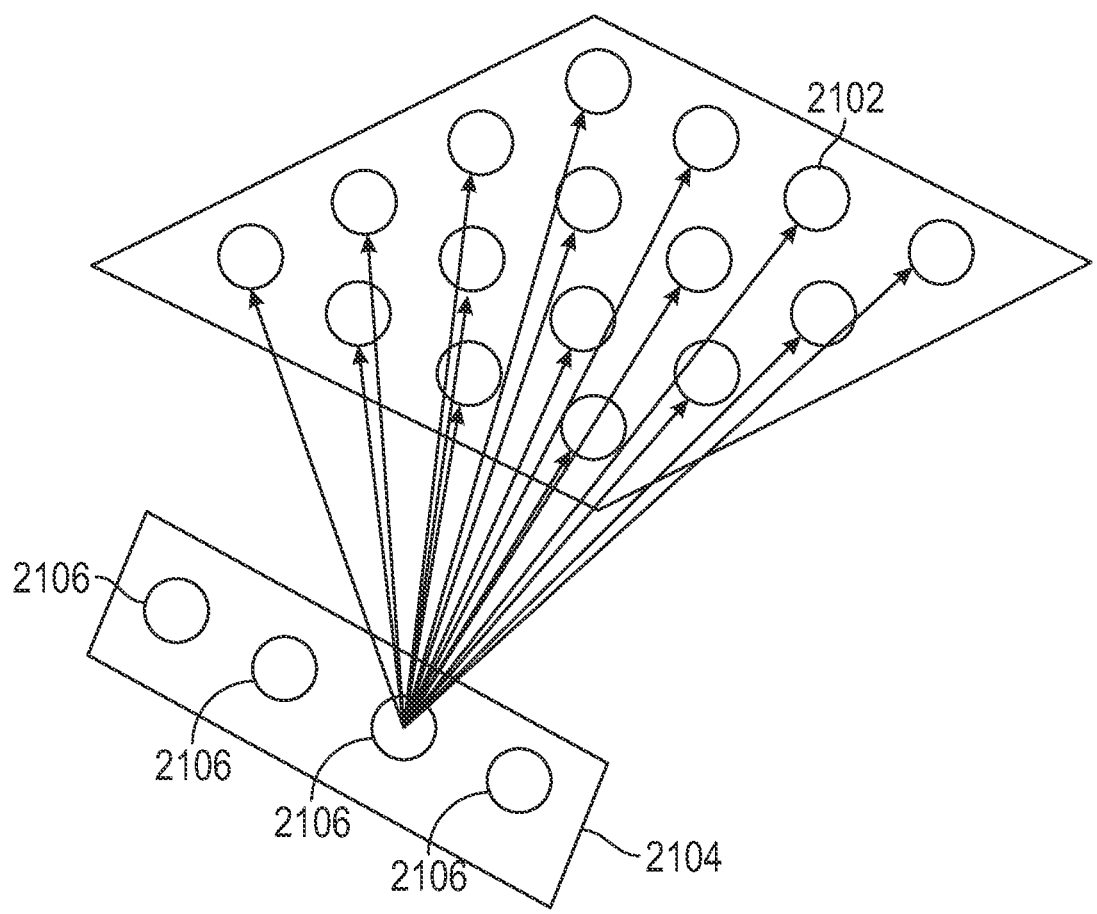
FIG. 23C is an illustration of how each node of the SOM network will contain the connection weights of the connections to all connected input nodes.

The server can also use unsupervised learning techniques as well as supervised learning techniques to determine the group or cluster to which particular events belong. Referring to FIGS. 23A-23B, a Self-Organizing Map (SOM) 2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101 (FIG. 23B). The specific number of inputs is dependent on the specifics of the data set. Each input node is connected to every node of the two (or three) dimensional SOM network (FIG. 23C) and each connection has a synaptic connection weight (w), much like that in supervised networks. Each node 2102 of the SOM network 2100 will contain the connection weights of the connections to all connected input nodes. As partially shown in FIG. 23C, each SOM network node 2102 is connected to all input nodes 2106, thus each node of the SOM network will have an equivalent number of connection weights (equivalent to the number of input nodes).

Figure 25:
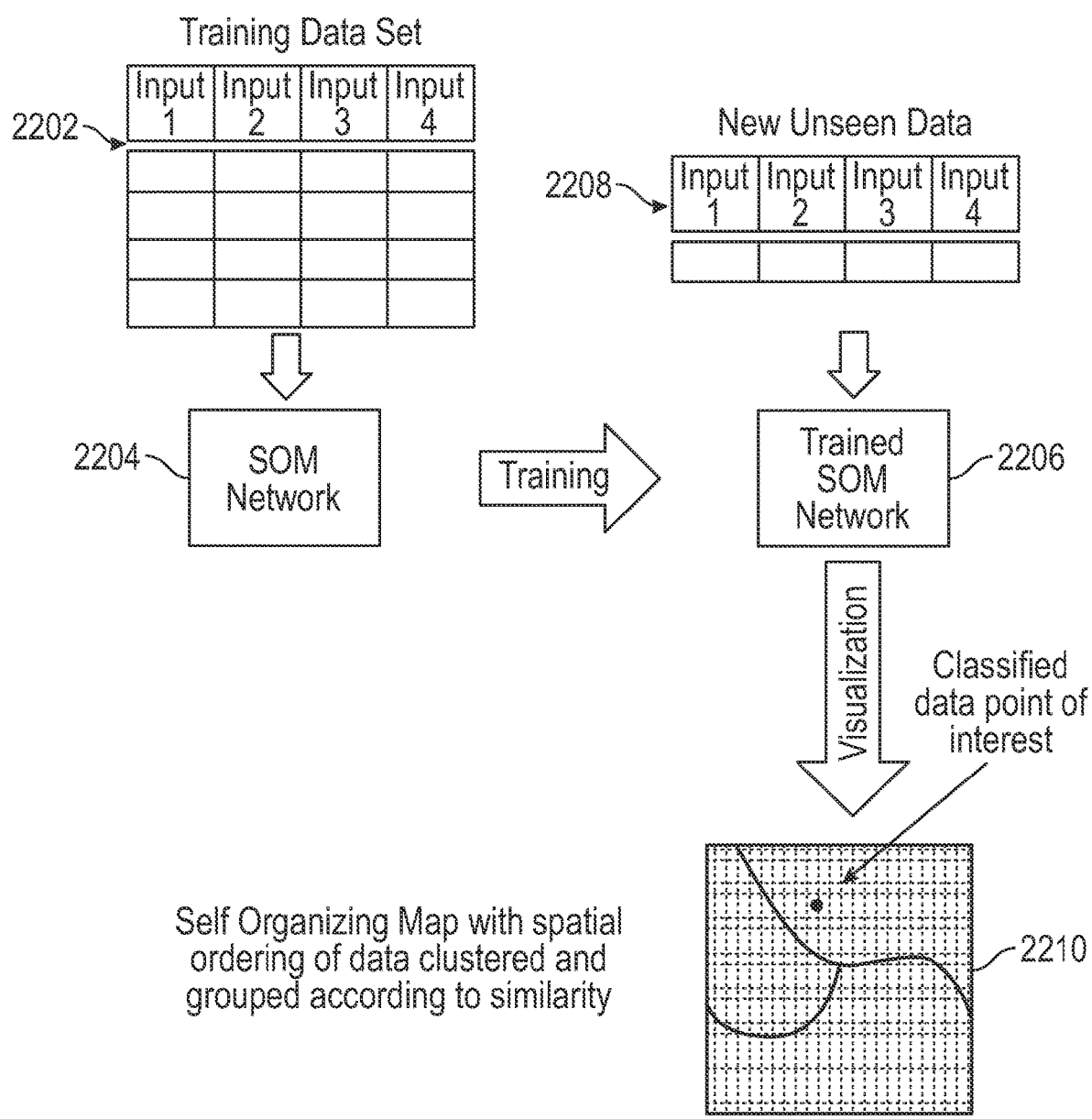
FIG. 25 is a block diagram illustrating high level operations of the process for training the SOM.

A representation of the process for creating, training and using the trained model is shown in FIG. 25. A training data set includes a plurality of attributes of past pick-up events. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. The SOM image 2210 can be rendered on a client device.

Figure 26:
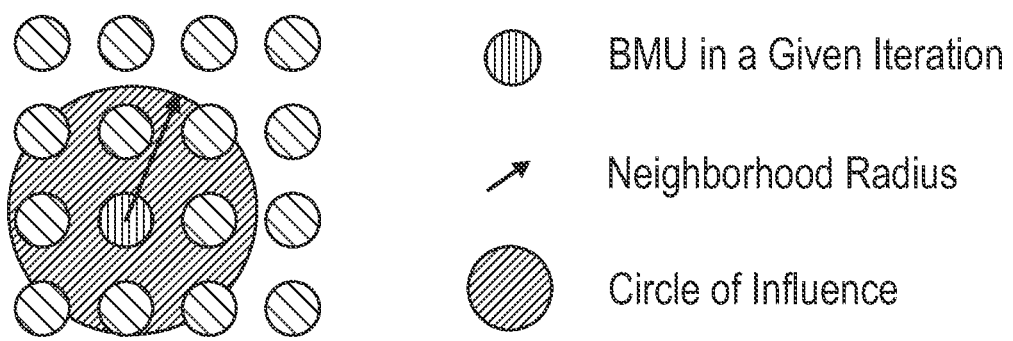
FIG. 26 is an illustration of the process for training the SOM network.

Referring to FIG. 26, the first step in SOM model training is to initialize values of the plurality of synaptic connection weights to random values. The next step is to randomly select one row (one past event) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closes to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n) = r_0 e^{-\left(\frac{n}{\lambda}\right)}$$

$r_0$=initial radius
n=iteration number
$\lambda$=time constant

Usually a large initial radius value is selected for the purpose of having almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1)=W_k(n)+\alpha(n)h_{ck}(n)[x(n)-W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n)-W_k(n)]$, the difference between $W_k(n)$, the old weights (the weights on the current training iteration), and $x(n)$, a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. So the learning rate and the influence factor decay over the period of iteration to allow for the proper convergence of the solution such that a stable result can be obtained at the end of training. The training process is repeated for a fixed number of N iterations to generate the trained SOM network.

Figure 24:
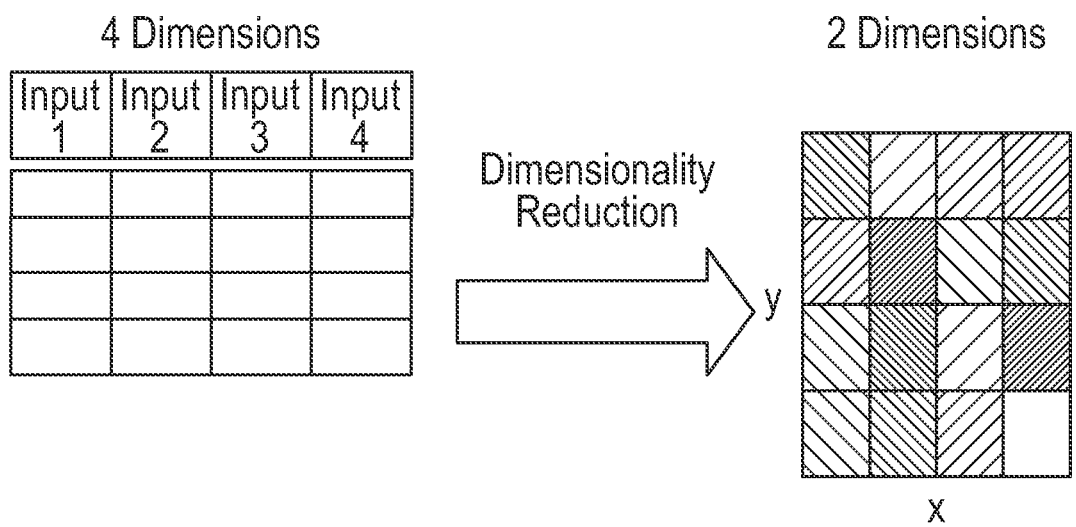
FIG. 24 is an illustration of the SOM network used to reduce dimensionality of the input data sets.

Returning to FIG. 13, an exemplary data set includes a plurality of data [1, 2 . . . N], and a number of properties [1, 2 . . . N] for each data. The data set can be a plurality of past pick-up request events and the properties can be a number of attributes of each past event. The high dimensionality of the data sets can make visualization of the data difficult. As illustrated in FIG. 24, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multidimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 27:
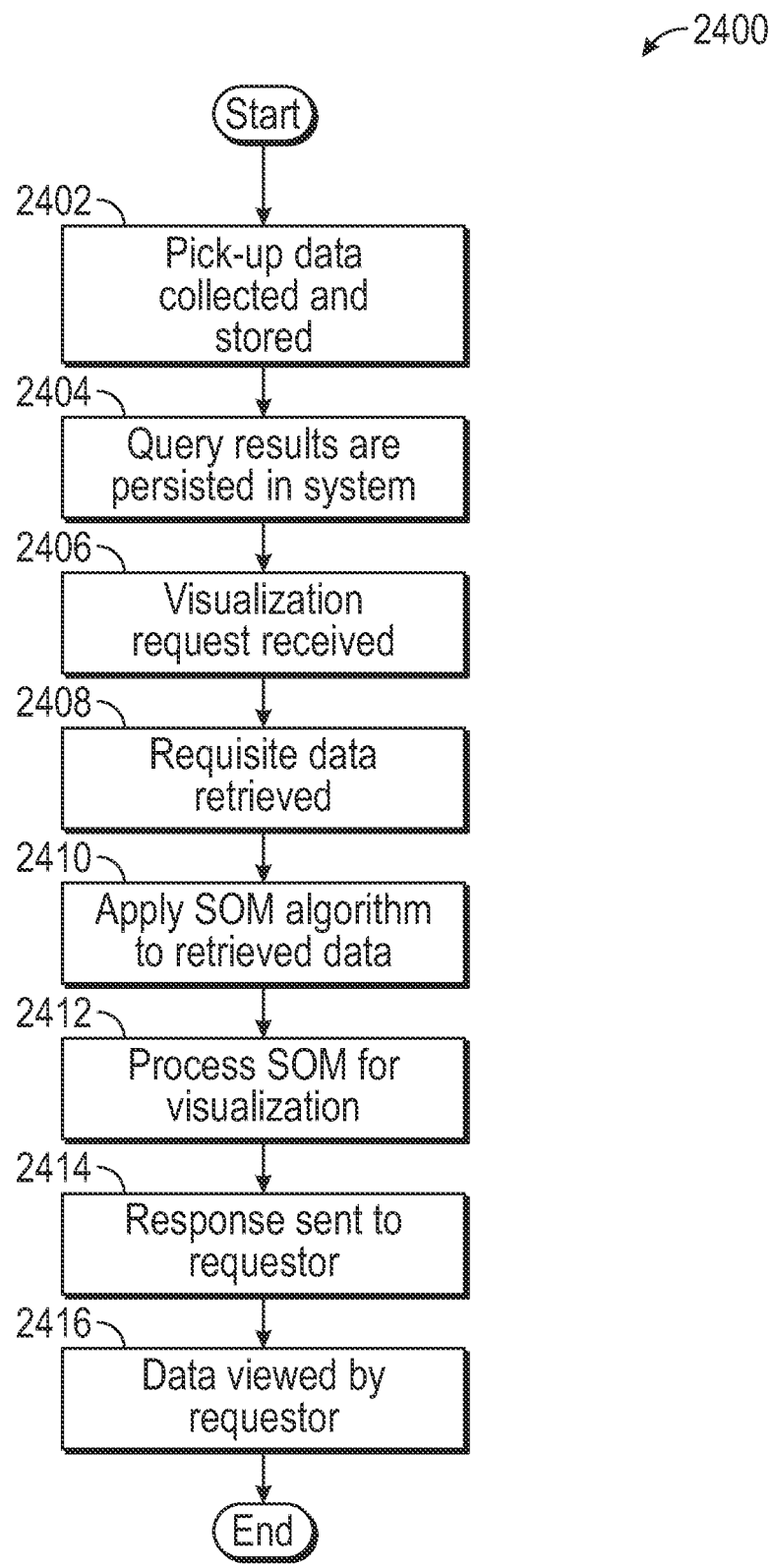
FIG. 27 is a flow diagram illustrating exemplary operations of the system to generate the graphical image including the visualization.

Referring to FIG. 27, an exemplary process 2400 by which the system can employ SOM network to take a data set of pick-up request events defined by n-dimensional input attributes and generate a visualization of the results after passing the data into a SOM network will be discussed. At 2402, pick-up request data is collected and stored. Particularly, the server collects the data from the vehicles in stores it in the database as discussed above. At 2404, the server (or TMD) can maintain query results in the memory. At 2406, the TMD receives a visualization request from a client device or web browser via the network with query parameters. At 2408, the TMD sends a data request with the query parameters to the server, which retrieves from the database the data sets consistent with the request. At 2410, the server inputs the data sets to the trained SOM network. At 2412, the server generates a visualization or graphical image based upon the output from the SOM network. At 2414, the server sends the graphical image to the TMD, which either sends it to the client device and/or renders the image on a display of a website. The output produced can be groupings or clustering of pick-up request events with similar characteristics, much like the classical "market segmentation" or "document classification" tasks for which SOMs are widely employed. This SOM output can be generated from a variety of vantage points or perspectives with one or more specified criteria, for example, specific time ranges, or for only deviated travel times, or only for a particular subset of pick-up requests handled by a particular driver/vehicle, a group of drivers/vehicles, a given region, or a particular requestor to name a few examples. SOM techniques can also be employed to predict the classification, type, or grouping of a particular pick-up request leveraging the attributes or inputs from an already existing data set of events, for example.

The backend devices (TMD and server) can use trained models such as the NNM and/or SOM to predict outputs corresponding to a present pick-up request event based upon past pick-up request events as described. The output values can be a travel path, a pick-up location for the pick-up request, and a price for the driver for the pick-up request and for the requestor. The input attributes for the pick-up request event can be: a number of the plurality of vehicles within the predetermined distance of the pick-up request; an identification for the driver of a particular vehicle (has this person accepted or refused a similar price in the past?); an identification for the originator of the pick-up request (has this person accepted or refused a similar price in the past?); a time of day and region.

The backend devices are capable of using their trained models to determine to which, if any, pick-up events can be charged more or less to the driver and the requestor (i.e. the backend devices can determine whether there is an opportunity, or more specifically, a high probability, of a requestor successfully accepting a higher price for a pick-up request or a driver accepting a lower price for a pick-up request). Particularly, to do this, the controller of the TMD may utilize a NNM that takes inputs such as deviation risk category (moderate or significant risk for delay) of the event, attributes of the pick-up request such as the time and location, etc.

In doing so, the TMD can determine whether (the probability that) pick-up events can be charged more or less to the driver and the requestor. Based on business logic and these results, the TMD may determine it does or does not recommend that the price be adjusted. There are a number of approaches the TMD could take to arrive at a decision. One demonstrative approach the TMD might take would be to recommend the deployment of an available resource if the probability weighted reduction in the predicted deviation exceeded a particular threshold. Those skilled in the art know there is a broad set of approaches that the system may take to make such recommendations and the approaches can further vary depending on the specific optimization objective(s). Moreover, while in practice the optimization technique employed may be more complex, the embodiment herein was selected to provide a simple demonstrative example of one of many potential optimization approaches the system might take. The r example herein is not intended to limit the scope of potential approaches to that described.

The performance metric, predictions, and other data generated by inventive system can be accessed via the backend device API and pulled into other third party user facing applications. The data can also be viewed by an authenticated and authorized end user in the graphical user interface of one of the system's client devices. Various views and transformations of the performance metric data can be provided.

The system enables its customers and end users to gain insights about their performance on various metrics of interest and to predict particular outcomes of interest. The customers/end users can slice the data and view it from perspectives that are of particular value to their organization. One benefit of the system is its ability to report relevant data it generates based on relationships between a plurality of related or unrelated workers and information in the system related to them over particular time ranges of interest. One of the system's client devices that communicates with the backend device can produce a dashboard tailored to the logged in end user's desired settings (i.e. which metrics to show, for what time ranges, etc.) and any restrictions thereof resulting from settings configured by authorized system administrators. End users can have saved views in addition to a system or user set default view. The end user can create ad hoc views as well and save them as saved views. The end user can interact with the dashboard to view the various metrics from different perspectives (drill up/drill down, change time range, view raw underlying data, etc.). The user can do this using various client device peripherals (touch screen, key board, mouse, microphone—voice commands .

. . . i.e. voice data that is streamed to a voice to text engine, transcribed, and interpreted by a machine, etc. For example a user could verbally "ask" that particular metric(s) of interest be fetched and shown in accordance with any criteria verbally provided and based upon parsing of the transcript returned, the system would attempt to fulfil the transcribed verbal request). One of the system's client devices can also be configured and used to operate a monitor or television (i.e. a large, flat screen monitor or TV). The client device's controller can run instructions native to the device or remotely received from the backend device to display data and metrics on the large screen graphical user interface. The client device may show a pre-defined sequence of metrics which loops and plays continuously or an authorized end user can interact with the client device via the large screen graphical interface. The large screen graphical user interface can be place in a secured area within an organization where access is controlled and only authorized personnel can enter and be used to communicate real time data and various performance metrics of interest that are being tracked by the system. The large screen graphical user interface can also be used and controlled by an authenticated and authorized end user during a meeting to display information or be used as a part of a virtual meeting (i.e. a web conference call).

The TMD or a client device running an application that communicates with the TMD can generate a graphical display which displays an average deviation percentage. Particularly, a client device can request this graphical display from the TMD or the underlying data required to generate it. The TMD can store the values or calculate them from data retrieved from the database of the server device.

While only certain features of the invention have been illustrated and described herein, many modifications and changes will occur to those of ordinary skill in the art. The following claims are intended to cover all such modifications and changes.

What is claimed is:

1. A server device for a transport service, the server device comprising:
    a transceiver configured to, via a network connection, receive:
        a plurality of messages associated with a plurality of vehicles, each of the plurality of messages indicative of location information; and
        a pick-up request indicative of location information associated with a user;
    a controller operatively coupled to the transceiver; and
    one or more memory sources operatively coupled to the controller, the one or more memory sources including instructions for configuring the controller to generate an output value from a trained model based upon the location information in the pick-up request and the location information in the plurality of messages associated with the plurality of vehicles,
    wherein the output value includes an arrival time,
    wherein the controller is further configured to determine a route from a specific one of the plurality of vehicles to the location information of the pickup-request.

2. The server device of claim 1, wherein the location information includes global positioning satellite coordinate information.

3. The server device of claim 1, wherein:
    the controller is further configured to generate an arrival time message including the arrival time; and
    the transceiver is further configured to send the arrival time message to the user.

4. The server device of claim 1, wherein the controller is further configured to generate an alert message to be sent to the user when the controller determines that the user is within a certain proximity to one or more of the plurality of vehicles based upon the plurality of messages and the pick-up request.

5. The server device of claim 1, wherein the server device is a central assignment system combined with one or more databases.

6. The server device of claim 1, wherein the server device is further configured to assign the specific one of the plurality of vehicles to the user based upon the output value.

7. The server device of claim 6, wherein the server device is further configured to generate an assignment message to be sent to the user informing the user of the assigned specific one of the plurality of vehicles and an expected time at which the vehicle will arrive at the location information associated with the pick-up request.

8. The server device of claim 1, wherein the output value is indicative of one of the plurality of vehicles and wherein the controller is further configured to track the user and the vehicle from an initial time of the pick-up request until the user arrives at a destination indicated in the pick-up request based upon the messages and the pick-up request.

9. The server device of claim 1, wherein:
    the controller is further configuring to:
        perform pre-processing on the location information as a plurality of input attributes to generate an input data set; and
        generate the output value from the trained model based upon the input data set,
    wherein the trained model includes one of a trained Self-Organizing Map (SOM) and a trained neural network model (NNM),
    wherein the trained SOM includes a plurality of network nodes arranged in a grid or lattice and in fixed topological positions, an input layer with a plurality of input nodes representing input attributes of past events, wherein each of the plurality of input nodes is connected to all of the plurality of network nodes by a plurality of synaptic weights; and
    wherein the trained NNM includes an input layer, output layer, and a plurality of hidden layers with a plurality of hidden neurons, wherein each of the plurality of hidden neurons includes an activation function, the activation function is one of:
    (1) the sigmoid function $f(x)=1/(1+e^{-x})$;
    (2) the hyperbolic tangent function $f(x)=(e^{2x}-1)/(e^{2x}+1)$; and
    (3) a linear function $f(x)=x$,
    wherein x is a summation of input neurons biased by synoptic weights.

10. The server device of claim 1, wherein:
    the transceiver further receives a drop-off request along with the pick-up request associated with the user, the drop-off request also indicative of another location information; and
    the output value is associated with one or more locations of interests within at least a predetermined distance from the location associated with the pick-up request or the another location associated with the drop-off request.

11. The server device of claim 1, wherein:
    the transceiver receives a plurality of present events, each including a plurality of input attributes, wherein the input attributes of each of the plurality of present events are the location information in the pick-up request and the location information in the plurality of messages associated with the plurality of vehicles;

the server is further configured to generate a graphical image including clusters of the input attributes for each of the plurality of present events;

the server receives a graphical display request from a remote client device and transmits the graphical image to the remote client device as a response; and the graphical image is a cluster diagram including a plurality of clusters of present events having a similar characteristic.

12. The server device of claim 1, wherein the trained model includes one of a trained Self-Organizing Map (SOM) and a trained neural network model (NNM).

13. A method for determining a location relating to a transport service on a computing device, the method being performed by one or more processors and comprising:

receiving a transport request from a user, the transport request specifying at least one of a pick-up region or a drop-off region;

determining one or more locations of interests within the at least one of the pick-up region or the drop-off region;

receiving a plurality of messages associated with a plurality of vehicles, each of the plurality of messages indicative of location information of the respective one of the plurality of vehicles;

generating one or more output values associated with difficulties of the plurality of vehicles of reaching each of the one or more locations of interest based upon a trained model, the determined one or more locations of interest and location information of the plurality of vehicles;

determining a specific one of the plurality of vehicles based upon the one or more output values; and determining a route from the specific one of the plurality of vehicles to the one or more locations of interest based upon the one or more output values.

14. The method of claim 13, further comprising inputting the determined one or more locations of interest and one or more historical locations related to the user into the trained model to generate the one or more output values.

15. The method of claim 13, wherein the trained model includes one of a trained Self-Organizing Map (SOM) and a trained neural network model (NNM).

16. A server device for a transport service, the server device comprising:

a transceiver configured to, via a network connection, receive:

a plurality of messages associated with a plurality of vehicles, each of the plurality of messages indicative of location information; and a pick-up request indicative of location information associated with a user and a destination request;

a controller operatively coupled to the transceiver; and one or more memory sources operatively coupled to the controller, the one or more memory sources including instructions for configuring the controller to generate output values from a trained model based upon the location information in the pick-up request and the location information in the plurality of messages associated with the plurality of vehicles, wherein one of the output values includes an arrival time one of the plurality of vehicles will arrive at the pick-up request, wherein the controller generates route information to be sent to the user via the transmitter so that a device at the user displays a travel path of the one of the plurality of vehicles to the pick-up request.

17. The server device of claim 16, wherein the controller is further generated to determine an optimal route from the pick-up request to the destination request based upon the trained model.

* * * * *